US012782273B2

(12) United States Patent
Cheng et al.

(10) Patent No.: US 12,782,273 B2
(45) Date of Patent: Nov. 3, 2026

(54) MOLECULAR PROBES FOR MAPPING BIOLOGICAL ACTIVITY

(71) Applicant: Trustees of Boston University, Boston, MA (US)

(72) Inventors: Ji-Xin Cheng, Newton, MA (US); Hongjian He, Waltham, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 18/424,524

(22) Filed: Jan. 26, 2024

(65) Prior Publication Data

US 2024/0255419 A1 Aug. 1, 2024

Related U.S. Application Data

(60) Provisional application No. 63/441,329, filed on Jan. 26, 2023.

(51) Int. Cl.

| | |
|---|---|
| ***G01N 21/35*** | (2014.01) |
| ***C12Q 1/42*** | (2006.01) |
| ***G01N 33/50*** | (2006.01) |
| ***G01N 33/58*** | (2006.01) |

(52) U.S. Cl.

CPC ......... *G01N 21/35* (2013.01); *G01N 33/5005* (2013.01); *G01N 33/581* (2013.01)

(58) Field of Classification Search

CPC .... G01N 21/35; G01N 33/581; G01N 21/171; G01N 2510/00; G01N 33/5005; C12Q 1/37; C12Q 1/42

See application file for complete search history.

(56) References Cited

U.S. PATENT DOCUMENTS

2009/0253143 A1 10/2009 Yang et al.
2022/0074861 A1 3/2022 Cheng et al.

FOREIGN PATENT DOCUMENTS

CN 112390872 B 6/2022

OTHER PUBLICATIONS

Li et al. Mid-Infrared Photothermal Imaging of Active Pharmaceutical Ingredients at Submicrometer Spatial Resolution. Anal. Chem. 2017;89:4863-4867.*

Bakthavatsalam et al. A decade of alkyne-tag Raman imaging (ATRI): applications in biological systems. RSC Chem. Biol. 2021;2:1415-1429.*

Arbeloa et al., "Photoresponse and anisotropy of rhodamine dye intercalated in ordered clay layered films," Journal of Photochemistry and Photobiology, vol. 8, pp. 85-108, 2007.

ATCC, "MIA PaCa-2," Retrieved from the Internet: <URL:https://web.archive.org/web/20221206043001/https://www.atcc.org/products/ctrl-1420>. p. 1, Dec. 2022.

Gao et al., "Imaging enzyme-triggered self-assembly of small molecules inside live cells," Nature Communications, vol. 3, No. 1033, pp. 1-8, Aug. 2012.

Romei et al., "Frequency Changes in Terminal Alkynes Provide Strong, Sensitive, and Solvatochromic Raman Probes of Biochemical Environments," The Journal of Physical Chemistry B, vol. 127, pp. 85-94, 2023.

Yin et al., "Nanosecond-resolution photothermal dynamic imaging via MHZ digitization and match filtering," Nature Communications, vol. 12, No. 7097, pp. 1-13, 2021.

International Search Report and Written Opinion issued in International Application No. PCT/US2024/013218 on May 24, 2024.

Aschaffenburg & Moog, "Probing Hydrogen Bonding Environments: Solvatochromic Effects on the CN Vibration of Benzonitrile," J. Phys. Chem. B, vol. 113, pp. 12736-12743, 2009.

Bai et al., "Bond-selective imaging by optically sensing the mid-infrared photothermal effect," Sci. Adv., vol. 7, pp. 1-13, 2021.

Bai et al., "Ultrafast chemical imaging by widefield photothermal sensing of infrared absorption," Sci. Adv., vol. 5, pp. 1-8, 2019.

Bao et al., "Charge and Hydrophobicity Effects of NIRFluorophores on Bone-Specific Imaging," Theranostics, vol. 5, Iss. 6, pp. 609-617, 2015.

Baruch et al., "Enzyme activity—it's all about image," Trends in Cell Biology, vol. 14, No. 1, pp. 29-35, 2004.

Brantley et al., "Discovery of small molecule inhibitors for the C. elegans caspase CED-3 by high-throughput screening," Biochemical and Biophysical Research Communications, vol. 491, pp. 773-779, 2017.

Buckingham, "Solvent effects in infra-red spectroscopy," Proceedings of the Royal Society of London. Series A. Mathematical and Physical Sciences pp. 169-182, 1958.

Carlile et al., "Caspase-3 has a nonapoptotic function in erythroid maturation," Blood, vol. 103, No. 11, pp. 4310-4316, 2004.

Chen et al., "Genomics and evolution of protein phosphatases," Sci. Signal, vol. 10, pp. 1-17, 2017.

Chyan & Raines, "Enzyme-Activated Fluorogenic Probes for Live-Cell and in Vivo Imaging," ACS Chem. Biol. vol. 13, pp. 1810-1823, 2018.

Gao et al., "Imaging Self-Assembly Dependent Spatial Distribution of Small Molecules in a Cellular Environment," Langmuir, vol. 29, pp. 15191-15200, 2013.

Grimm et al., "The Chemistry of Small-Molecule Fluorogenic Probes," Progress in Molecular Biology and Translational Science, vol. 113, pp. 1-34, 2013.

(Continued)

*Primary Examiner* — Lynn Y Fan

(74) *Attorney, Agent, or Firm* — Cesari and McKenna, LLP; Steven M. Mills

(57) ABSTRACT

A system and method for characterizing biological activity in a live cell using a mid-infrared photothermal system and at least one molecular probe. A mid-infrared optical source generates a mid-infrared beam, the mid-infrared beam being directed at the sample to induce a thermal effect. A visible light source generates a light, the light illuminating the sample on the substrate. An optical detector collects the light after interaction with the sample. Biological activity in the sample is characterized based on a spectral shift. Each molecular probe includes an substrate and a chemical functional group.

16 Claims, 35 Drawing Sheets

(56) References Cited

OTHER PUBLICATIONS

Guo et al., "The ratio of hydrogelator to precursor controls the enzymatic hydrogelation of a branchedpeptide," Soft Matter, vol. 16, pp. 10101-10105, 2020.
Halle et al., "Caspase-3 Regulates Catalytic Activity andScaffolding Functions of the Protein TyrosinePhosphatase PEST, a Novel Modulator of the Apoptotic Response," Molecular and Cellular Biology, vol. 27, No. 3, pp. 1172-1190, 2007.
Halle et al., "Protein Tyrosine Phosphatases: EmergingRegulators of Apoptosis," Cell Cycle, vol. 6, No. 22, pp. 2773-2781, 2007.
Hamilton et al., "Mapping Enzyme Activity on Tissue by Functional Mass Spectrometry Imaging," Angew. Chem., vol. 132, pp. 3883-3886, 2020.
He et al., "Branched peptides for enzymatic supramolecular hydrogelation," Chem. Commun., vol. 54, pp. 86-89, 2018.
He et al., "Enzymatic Noncovalent Synthesis," Chem. Rev., vol. 120, pp. 9994-10078, 2020.
Heath, "The Effects of Substituents on the Rates of Hydrolysis of Some Organophosphorus Compounds. Part I. Rates in Alkaline Solution," Journal of the Chemical Society (Resumed), pp. 3796-3804, 1956.
Johnson et al., "Dysregulation of Glutathione Homeostasis in Neurodegenerative Diseases," Nutrients, vol. 4, pp. 1399-1440, 2012.
Johnson et al., "Strategies for discovering and derisking covalent, irreversible enzyme inhibitors," Future medicinal chemistry, vol. 2, pp. 949-964, 2010.
Kim & Xu, "Enzyme-Instructed Self-Assembly for Cancer Therapy and Imaging," Bioconjugate Chem., vol. 31, pp. 492-500, 2020.
Klumpp & Krieglstein, "Serine/threonine protein phosphatases in apoptosis," Current opinion in pharmacology, vol. 2, pp. 458-462, 2002.
Kwan et al., "Self-Immobilizing Fluorogenic Imaging Agents of Enzyme Activity," Angew. Chem., vol. 123, pp. 314-317, 2011.
Liu et al., "In Situ Localization of Enzyme Activity in Live Cells by a Molecular Probe Releasing a Precipitating Fluorochrome," Angew. Chem. Int. Ed., vol. 56, pp. 11788-11792, 2017.
Matsuo et al., "Specific Detection and Imaging of Enzyme Activity by Signal-Amplifiable Self-Assembling 19F MRI Probes," Chem. Eur. J., vol. 19, pp. 12875-12883, 2013.
Mohamed & Sloane, "Cysteine cathepsins: multifunctional enzymes in cancer," Nature Reviews Cancer, vol. 6, pp. 764-775, 2006.
Noe & Gilbert, "Targeted Covalent Enzyme Inhibitors," Annual Reports in Medicinal Chemistry, vol. 47, pp. 413-439, 2012.
Razgulin et al., "Strategies for in vivo imaging of enzyme activity: an overview and recent advances," Chem. Soc. Rev., vol. 40, pp. 4186-4216, 2011.
Shi et al., "Mid-infrared metabolic imaging with vibrational probes," Nature Methods, vol. 17, pp. 844-851, 2020.
Sreedhar & Zhao, "Dysregulated metabolic enzymes and metabolic reprogramming in cancer cells (Review)," Biomedical Reports, vol. 8, pp. 3-10, 2018.
Stergiou et al., "The nucleotide excision repair pathway is required for UV-C-induced apoptosis in Caenorhabditis elegans," Cell Death and Differentiation, vol. 14, pp. 1129-1138, 2007.
Sztiller-Sikorska et al., "A non-apoptotic function of caspase-3 in pharmacologically-induced differentiation of K562 cells," British Journal of Pharmacology, vol. 157, pp. 1451-1462, 2009.
Tai et al., "Detecting nitrile-containing small molecules by infrared photothermal microscopy," Analyst, vol. 146, pp. 2307-2312, 2021.
Torres et al., "Phosphorylation-regulated Cleavage of the Tumor Suppressor PTEN by Caspase-3," The Journal of Biological Chemistry, vol. 278, No. 33, pp. 30652-30660, 2003.
Van Hoof et al., "Phosphatases in apoptosis: to be or not to be, PP2A is in the heart of the question," Biochimica et Biophysica Acta, vol. 1640, pp. 97-104, 2003.
Wang et al., "Aggregation Enhanced Responsiveness of Rationally Designed Probes to Hydrogen Sulfide for Targeted Cancer Imaging," J. Am. Chem. Soc., vol. 142, pp. 15084-15090, 2020.
Wei et al., "Live-cell imaging of alkyne-tagged small biomolecules by stimulated Raman scattering," Nature Methods, vol. 11, No. 4, pp. 410-414, 2014.
Wei et al., "Super-multiplex vibrational imaging," Nature, vol. 544, pp. 465-483, 2017.
Wilhelm et al., "Activation of caspase-3-like enzymes in nonapoptotic T cells," Eur. J. Immunol. vol. 28, pp. 891-900, 1998.
Xia et al., "Mid-Infrared Photothermal Microscopy: Principle, Instrumentation, and Applications," J. Phys. Chem. B, vol. 126, pp. 8597-8613, 2022.
Xing et al., "Cell-Permeable Near-Infrared Fluorogenic Substrates for Imaging B-Lactamase Activity," J. Am. Chem. Soc., vol. 127, pp. 4158-4159, 2005.
Yang et al., "Elevated B-secretase expression and enzymatic activity detected in sporadic Alzheimer disease," Nature Medicine, vol. 9, No. 1, pp. 3-4, 2003.
Yang et al., "Protein Tyrosine Phosphatase Regulation of Endothelial Cell Apoptosis and Differentiation," Cell Growth & Differentiation, vol. 7, pp. 161-171, 1996.
Zanetti-Domingues et al., "Hydrophobic Fluorescent Probes Introduce Artifacts into Single Molecule Tracking Experiments Due to Non-Specific Binding," PLOS One, vol. 8, Iss. 9, pp. 1-11, 2013.
Zhang et al., "Depth-resolved mid-infrared photothermal imaging of living cells and organisms with submicrometer spatial resolution," Sci. Adv., vol. 2, pp. 1-7, 2016.
Zhang et al., "Fluorescence-Detected Mid-Infrared Photothermal Microscopy," J. Am. Chem. Soc., vol. 143, pp. 11490-11499, 2021.
Zhang et al., "Fluorogenic probes for disease-relevant enzymes," Chem. Soc. Rev., vol. 48, pp. 683-722, 2019.
Zhou et al., "Enzyme-Instructed Self-Assembly for Spatiotemporal Profiling of the Activities of Alkaline Phosphatases on Live Cells," Chem, vol. 1, pp. 246-263, 2016.

* cited by examiner

Casp-CN(S)

202

Casp-CN(P)

204

206

Phos-CN(S)

Phos-CN(P)

208

546

548

MOLECULAR PROBES FOR MAPPING BIOLOGICAL ACTIVITY

CROSS REFERENCE TO RELATED APPLICATIONS

This application claims priority to and the benefit of U.S. Provisional Patent Application No. 63/441,329, filed on Jan. 26, 2023, and entitled "NOVEL NITRILE PROBES AND USES THEREOF", the contents of which are incorporated herein by reference as though fully set forth herein.

GOVERNMENT SUPPORT

This invention was made with government support under Grant number R35GM136223, awarded by the National Institutes of Health. The Government has certain rights in this invention.

FIELD OF THE TECHNOLOGY

The subject disclosure relates to mapping biological activity using a mid-infrared photothermal (MIP) imaging system.

BACKGROUND OF THE TECHNOLOGY

Enzymes, efficient and specific catalysts of a variety of biochemical reactions, play critical roles in literally all biological processes. Precise spatial and temporal regulation of enzyme activity is crucial to the successful operation of cellular machineries. Thus, it is significant to spatially map and quantify the activity of enzymes, preferentially in living organisms for understanding the functions and roles of enzymes in health and disease. Notably, many biological events and signaling pathways, such as apoptosis, are accomplished by the cooperation of multiple enzyme species. Clearly, the attempts to map the activity of one kind of enzyme in one area of intertest (AOI) is insufficient to understand the cooperation among different enzymes in a complicated biological system. This gap urges the development of approaches that are capable of spatially profiling the activity of different enzymes in the same AOI at single cell level and in vivo for elucidating the links of multiple enzymes to life and pathophysiological processes.

Visualizing enzyme activity is largely performed by synthetic fluorogenic substrates. However, current fluorogenic probes fail to provide spatial information because the water-soluble fluorophores tend to diffuse away from the reaction sites. Recently, self-immobilizing fluorogenic reporters have been developed to locate enzyme activities in dynamic environments. However, the covalent connection of bulky fluorophores to enzymes increase the risk of perturbing the function of the enzymes and consequently disrupting the downstream signaling and cellular activity. Thus, the potential enzyme-silencing effects of self-immobilizing strategy diminish its application for mapping the activities of multiple enzymes in living systems.

A further development of fluorescent probes to profile enzyme activity in living organisms derive from in-situ enzymatic noncovalent synthesis (ENS) of small molecules into non-diffusive nanostructures to allow the retention of fluorescent modalities at reaction sites. Notably, the characteristics of fluorophores are critical to a successful mapping of enzyme activity via ENS-based fluorescent probes. These filter criteria largely reduce the scope of fluorophore candidates. Given the broad-band emission spectrum, current research using this strategy mostly focuses on the mapping of one kind of enzyme in one AOI, which is barely enough to elucidate the cooperation between different enzymes in a biological process.

Beyond fluorescence, other technologies have been developed to map enzyme activity in cells and tissues, including magnetic resonance imaging (MRI) and mass spectrometry imaging (MSI). However, poor spatial resolution or inapplicability to living organisms significantly restrict these approaches towards high-resolution mapping of the activity of multiple enzymes in living subjects.

SUMMARY OF THE TECHNOLOGY

Addressing these challenges requires innovations in imaging systems and in chemistry. In light of the needs described above, in at least one aspect, the subject disclosure relates to a method for visualizing enzyme activities via real-time mid-infrared photothermal (MIP) imaging of a category of nitrile-tagged enzyme activity probes. The recently developed MIP microscope enables chemical imaging with submicron spatial resolution by sensing the photothermal effect induced by mid-infrared absorption with a visible light. Importantly, such indirect measurement mitigates the huge water absorption issue and allows mid-infrared imaging in aqueous environment with high contrast. The reported sample-scan MIP microscope needs a pixel dwell time ranging from 500 us to 10 ms, making it difficult to resolve the movements of living systems. To address these difficulties, we have developed a laser-scan MIP microscope with high speed and high sensitivity. In this new system, a synchronized laser scanning scheme is exploited for high-speed imaging, enabling a pixel dwell time as short as a few microseconds. These efforts collectively allow real-time MIP imaging of living systems.

While label-free MIP microscopy succeeds in visualizing the abundant cellular components, direct observation of specific enzymatic reactions in cells/tissues remains difficult because the MIP signals from products are immersed into the strong background from other biomolecules. To address this challenge, we synthesized a kind of nitrile-tagged bio-orthogonal enzyme activity probes. The vibration frequency of the nitrile group (C≡N) differs from those of endogenous functional groups, thus exhibiting unique IR absorbance in the cell-silent region. The C≡N group has a relatively large infrared absorption cross-section and can serve as a sensitive photothermal reporter. Spectrally, the C≡N vibration is narrowband and tunable through chemical and physical approaches, enabling super-multiplexed detection. Thus, adopting C≡N as a photothermal reporter of biochemical reaction is promising for bio-orthogonal detection of multiple enzyme activities in living systems. Here, we synthesized a series of nitrile-tagged enzyme activity probes, named nitrile chameleons. The probes exhibit reaction-activatable MIP spectral shifts of C≡N which signifies enzymatic reactions. These probes also perform in-situ ENS for mapping enzyme activity.

BRIEF DESCRIPTION OF THE DRAWINGS

So that those having ordinary skill in the art to which the disclosed system pertains will more readily understand how to make and use the same, reference may be had to the following drawings.

DETAILED DESCRIPTION

Figure 1B:
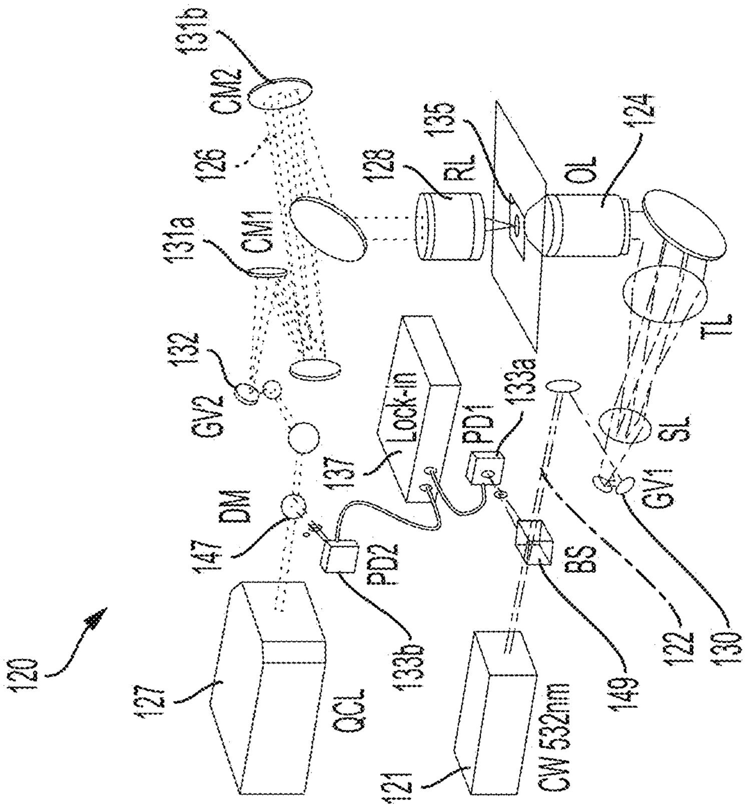
FIG. 1*b* is a schematic illustration of an MIP microscope, in accordance with the subject technology.

The subject technology overcomes many of the prior art problems associated with imaging systems using MIP microscopy. The advantages, and other features of the systems and methods disclosed herein, will become more readily apparent to those having ordinary skill in the art from the following detailed description of certain preferred embodiments taken in conjunction with the drawings which set forth representative embodiments of the present invention. Like reference numerals are used herein to denote like parts. Further, words denoting orientation such as “upper”, “lower”, “distal”, and “proximate” are merely used to help describe the location of components with respect to one another. For example, an “upper” surface of a part is merely meant to describe a surface that is separate from the “lower” surface of that same part. No words denoting orientation are used to describe an absolute orientation (i.e. where an “upper” part must always at a higher elevation).

Figure 1A:
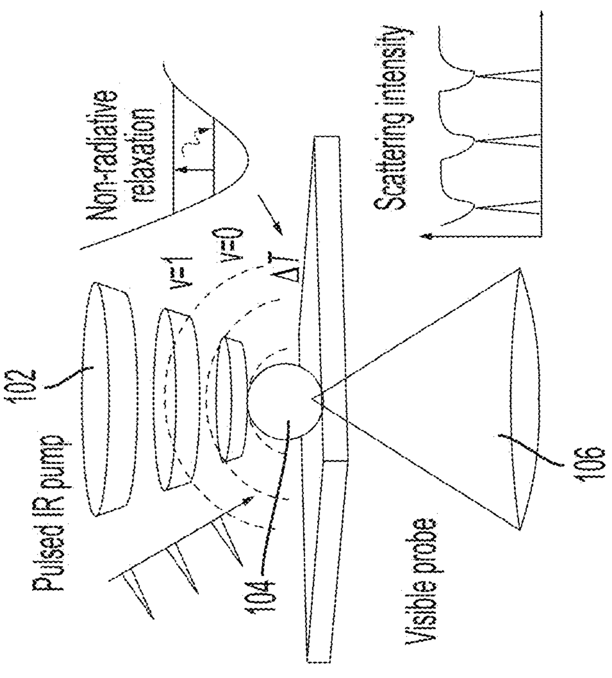
FIG. 1*a* is a schematic illustration of the principles of MIP detection.
Figure 1C:
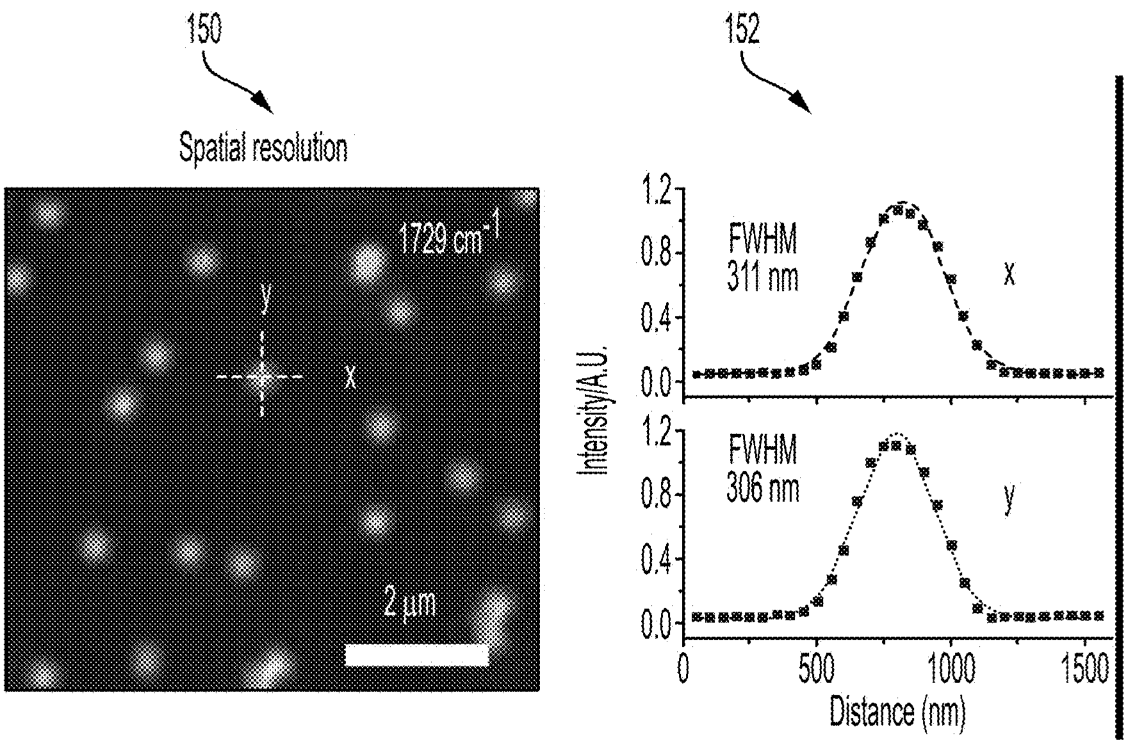
FIG. 1*c* shows an image and graph of the spatial resolution characterization of 200-nm diameter PMMA particles.
Figure 1D:
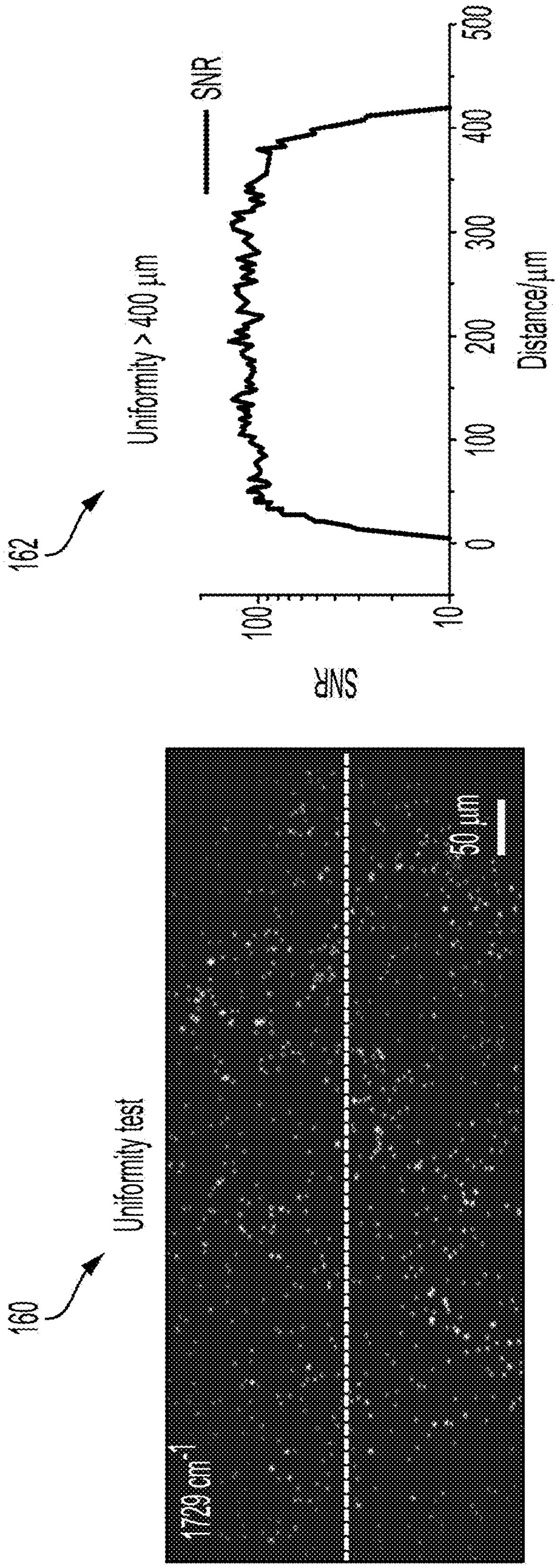
FIG. 1*d* shows an MIP image and graph showing uniform characterization of 500-nm diameter PMMA particles.
Figure 1E:
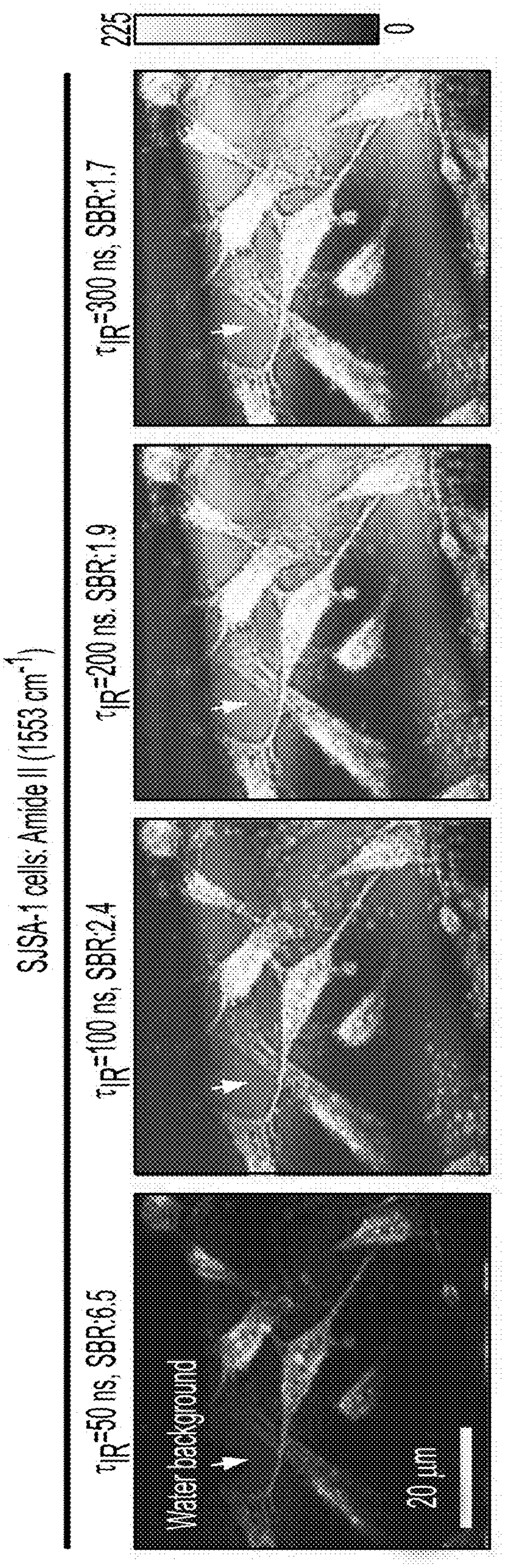
FIG. 1*e* shows MIP images of proteins in cancer cells with different IR excitation pulse width.
Figure 1F:
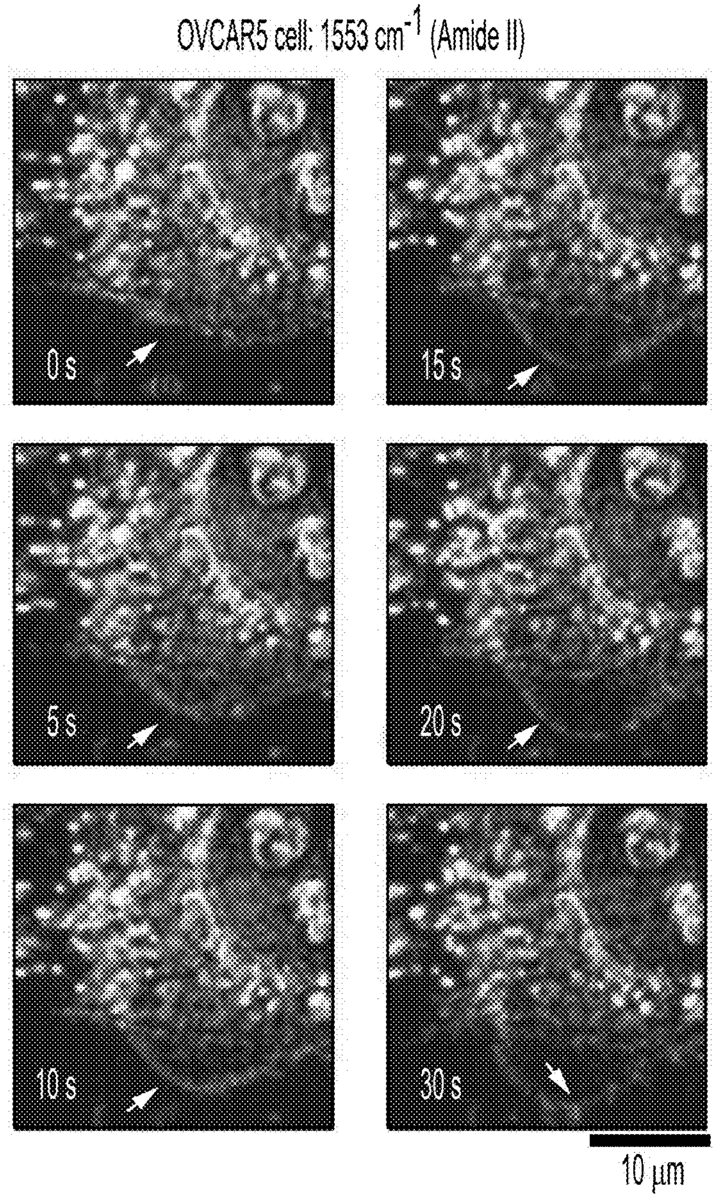
FIG. 1*f* shows images of live cell MIP imaging of protein dynamics (1553 $cm^{-1}$, amide II) in cancer cells.

Referring now to FIGS. 1*a*-1*f*, images related to a laser-scan mid-infrared photothermal (MIP) microscope for real-time bond-selective imaging of living cells at 300-nm spatial resolution are shown. In particular, FIG. 1*a* shows the principles of MIP detection, while FIG. 1*b* shows a schematic illustration of an MIP microscope 120. FIG. 1*c* shows an image 150 and graph 152 of the spatial resolution characterization of 200-nm diameter PMMA particles. FIG. 1*d* shows an MIP image 160 and graph 162 showing uniform characterization of 500-nm diameter PMMA particles. FIG. 1*e* shows MIP images of proteins in cancer cells with different IR excitation pulse width. FIG. 1*f* shows images of live cell MIP imaging of protein dynamics (1553 $cm^{-1}$, amide II) in cancer cells. The results shown in these images were also recreated with similar results.

More particularly, in FIG. 1*a*, a mid-infrared light 102 excites the chemical bond through vibrational transition. The vibrational energy is deposited into the sample 104 which subsequently experiences a local temperature rise. The temperature escalation introduces several photothermal effects such as thermal expansion and refractive index alteration. Those changes influence the scattering of a visible probe 106, which is adopted as the photothermal signal.

Referring now to FIG. 1*b*, an exemplary laser-scan MIP microscope 120 for imaging a living sample 135 is built on an inverted microscope frame (e.g. IX73, Olympus). A visible probe 122 is provided by a continuous-wave 532 nm laser (121, e.g. Samba, HUBNER photonics). A mid-infrared pump 126 is provided by a pulsed quantum cascade laser (127, e.g. MIRcat 2400, Daylight Solutions) tunable from 900 $cm^{-1}$ to 2300 $cm^{-1}$. The visible beam 122 is scanned by a galvo mirror 130 with 3 mm aperture (e.g. Saturn 1B, ScannerMax) and focused with a water immersion objective lens 124 (e.g. 1.2NA, 60×, Olympus). The IR beam 126 is synchronously scanned with another pair of galvo mirrors 132 (e.g., GVS001, Thorlabs) and focused on the same spot with a reflective objective 128 (e.g. 0.5NA, 40×, Thorlabs). For IR beam scanning, reflective conjugation with two concave mirrors 131*a*, 131*b* is used for removing the chromatic aberration. Probe photonics are collected in both forward and backward directions by photodiodes 133*a*, 133*b*, using a dichroic mirror 147 and beam splitter 149 to redirect light along the collection paths. In one example, their intensity is sensed by silicon photodiodes 133*a*, 133*b* (e.g. DET100A, Thorlabs) connected with low-noise amplifier (e.g. SA230, NF cooperation). The amplifier signal is then sent to a lock-in amplifier 137 (e.g. HF2LI, Zurich) for MIP signal demodulation. The microscope 120 can be controlled by computer connected to software, such as Lab View 2020.

It should be understood that other typical optical components (e.g. lenses, mirrors) and/or electrical components (power supplies, amplifiers, processing equipment) may be included to allow the microscope 120 to function as described herein. Further, the various components of the microscope 120 can be implemented using different components than those particularly shown and described, as would be understood by one of skill in the art.

Previous MIP microscopes relied on sample scan with a pixel dwell time of 500 us or longer, which is insufficient in capturing the dynamics a living system. To increase the MIP imaging speed, we designed a laser-scan MIP microscope 120 (FIG. 1*b*) that provides a much faster pixel resolving speed on the order of a few microseconds. With such speed, it enables visualization of fast dynamics in real-time (20 Hz) at a small range with pixel counts under 25,000 (158×158). For providing high spatial resolution, counter-propagating geometry is applied to the microscope. Specifically, the visible beam 122 is focused via a water immersion objective lens 124 with 1.2 NA, while the infrared (IR) beam 126 is focused by a reflective objective 128 with 0.5 NA. The spatial resolution is characterized by imaging of PMMA particles with 200 nm diameter (FIG. 1*c*). The resolution reached 300 nm, approaching a theoretical resolution of 276 nm which was estimated from point spread function. The vertical resolution is determined to be 640 nm, resulting in a voxel as a cube with lateral dimensions of 300 nm and axial dimensions of 640 nm. By synchronously scanning IR and visible beams 126, 122 with two pairs of galvo mirrors (130, 132), a uniform field of view over 400 μm is reached (FIG. 1*d*).

For live cell imaging, we optimized the IR excitation pulse width to maximize the signal to water background ratio. The photothermal dynamics of the water background is known to have a large decay constant (TB) due to the large heat capacity. The decay constant ($\tau_s$) for the signal from organelles is usually smaller. We harness this difference to enhance the signal to background contrast by reducing the heating pulse duration t. Experimentally, we compared the influence of heating pulse duration on the MIP contrast of a live cell at the protein channel (1553 $cm^{-1}$, amide II). Results show that a pulse duration of 50 ns provides the highest SBR with negligible photodamage (FIG. 1*e*). Thus, we demonstrated live cell MIP imaging at the protein channel (1553 $cm^{-1}$, FIG. 1*f*) and kept the conditions for the following experiments unless specifically noted.

Figure 2A:
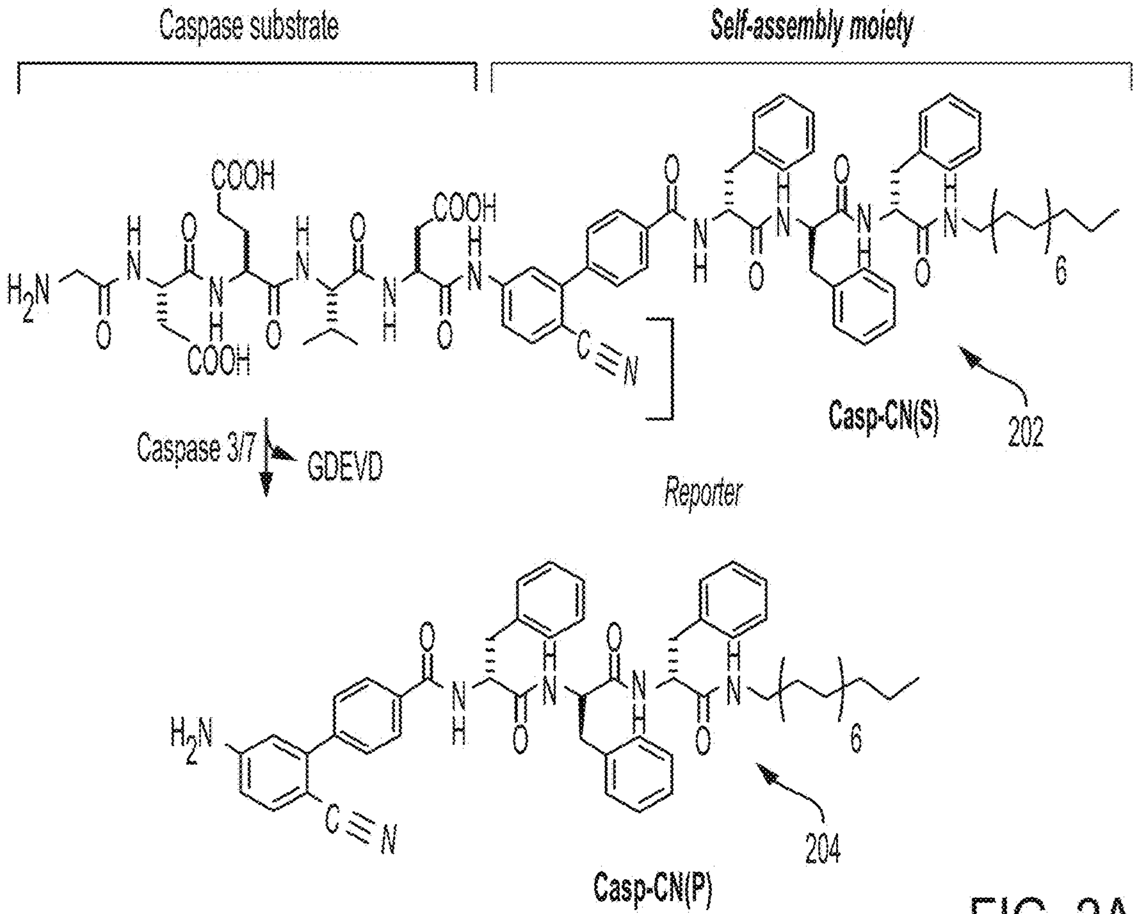
FIG. 2*a* shows molecular structures of Casp-CN(S) and the enzymatic product Casp-CN(P).
Figure 2B:
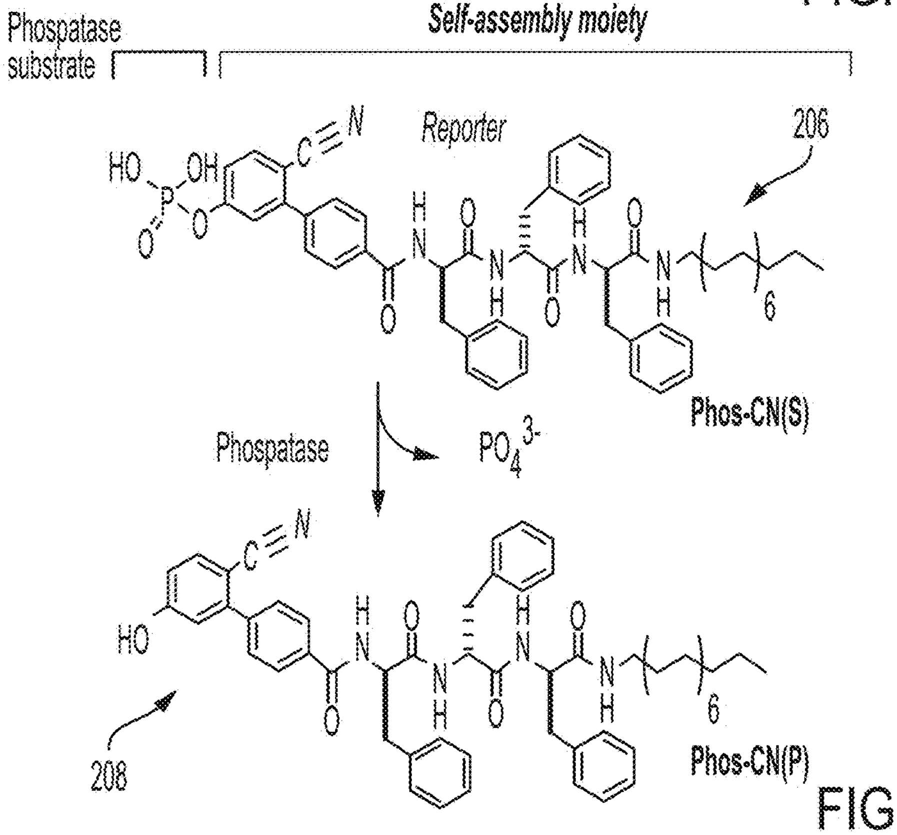
FIG. 2*b* shows molecular structures of Phos-CN(S) and the enzymatic product Phos-CN(P).
Figure 2D:
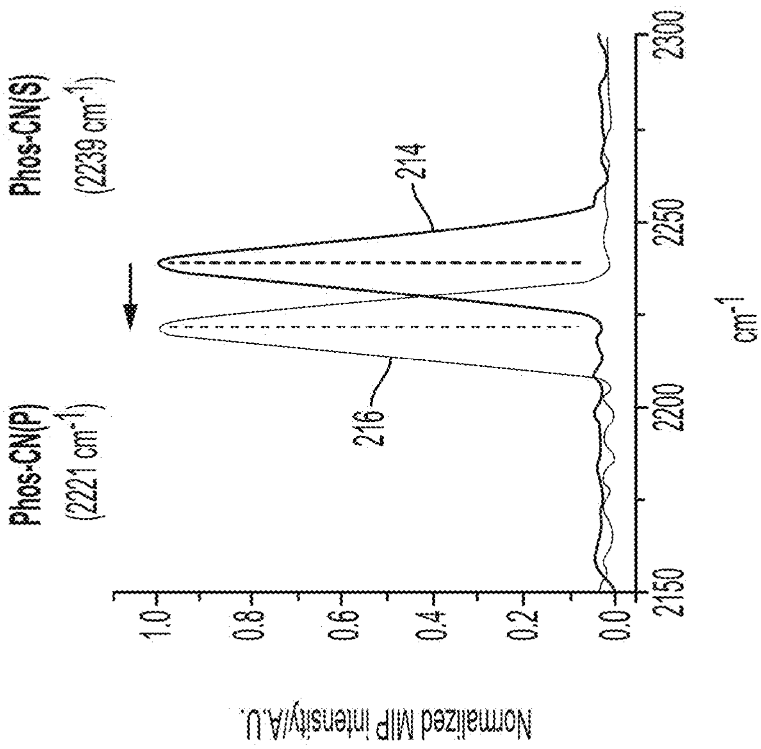
FIG. 2*d* is a graph of MIP spectra of Phos-CN(S) and the enzymatic product Phos-CN(P), 50 mM in DMSO.
Figure 2C:
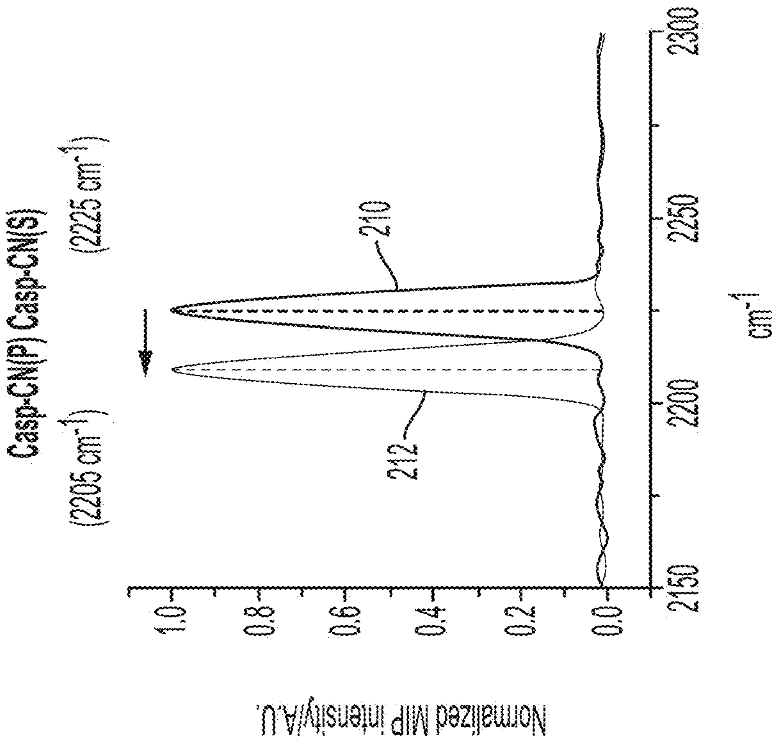
FIG. 2*c* is a graph of MIP spectra of Casp-CN(S) and the enzymatic product Casp-CN(P), 50 mM in DMSO.
Figure 2G:
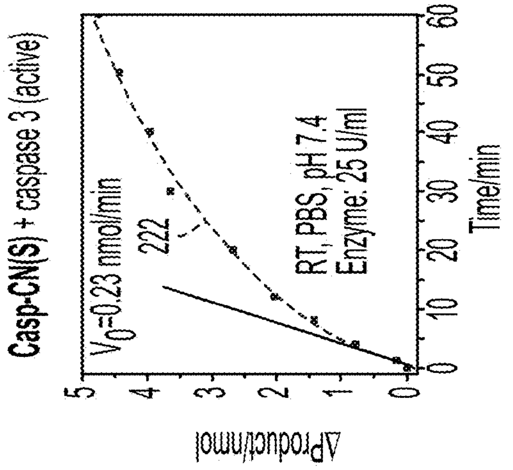
FIG. 2*g* is a graph showing time-dependent formation of Casp-CN(P) catalyzed by active caspase 3 (25μ/mL).
Figure 2F:
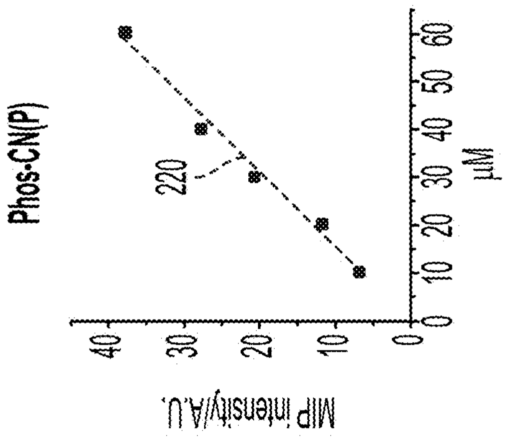
FIGS. 2*e*-2*f* are graphs of MIP signal intensity of Casp-CN(P) and Phos-CN(P), respectively, at different concentration concentrations in DMSO.
Figure 2E:
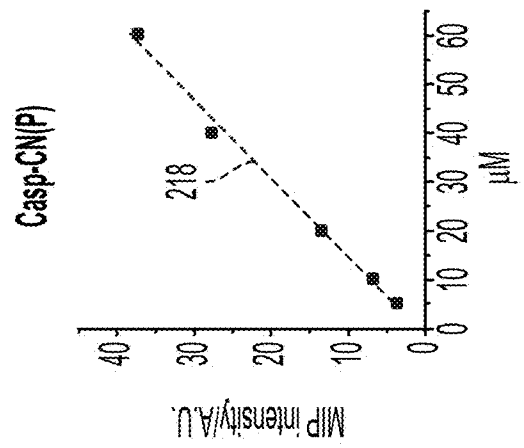
Figure 2J:
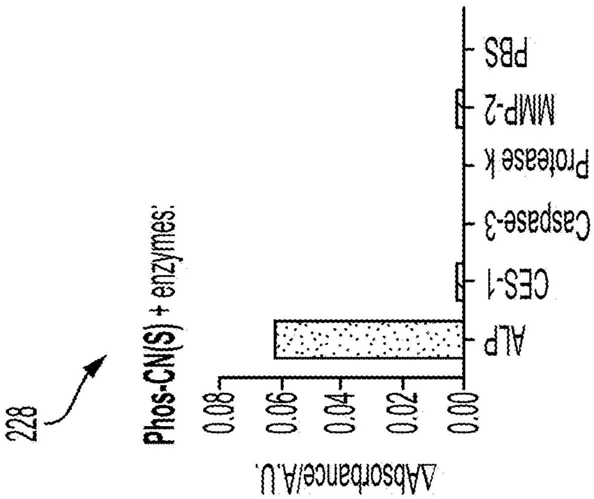
FIGS. 2*i*-2*j* are graphs of UV absorbance changes in the mixtures of Casp-CN(S) and Phos-CN(S), respectively, with PBS, ALP, caspase-3 (active), carboxylesterase-1 (CES-1), matrix metalloproteinase-2 (MMP-2), and proteinase K.
Figure 2I:
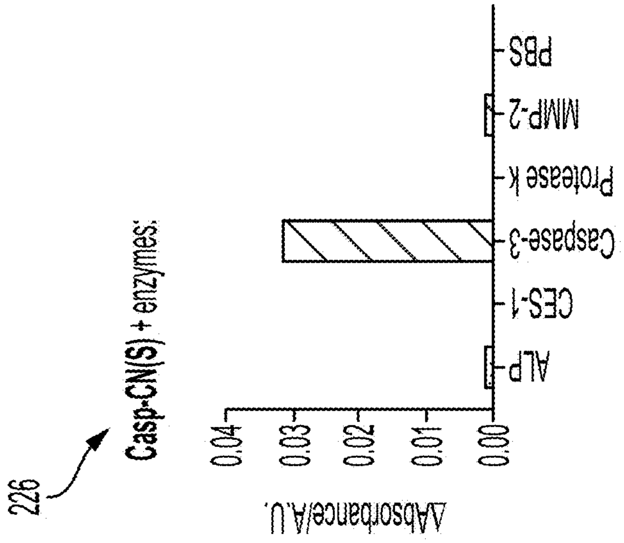
Figure 2H:
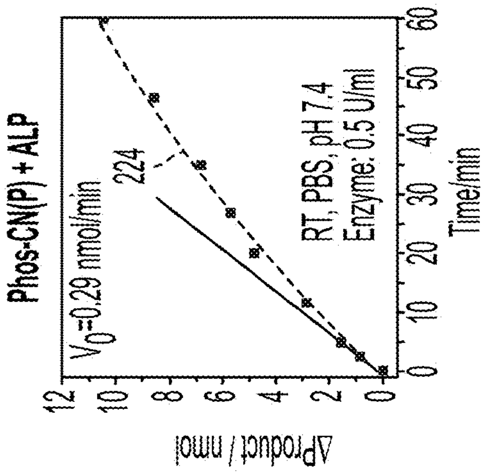
FIG. 2*h* is graph of time-dependent formation of Phos-CN(P) catalyzed by alkaline phosphatase (ALP, 0.5μ/mL).
Figure 2K:
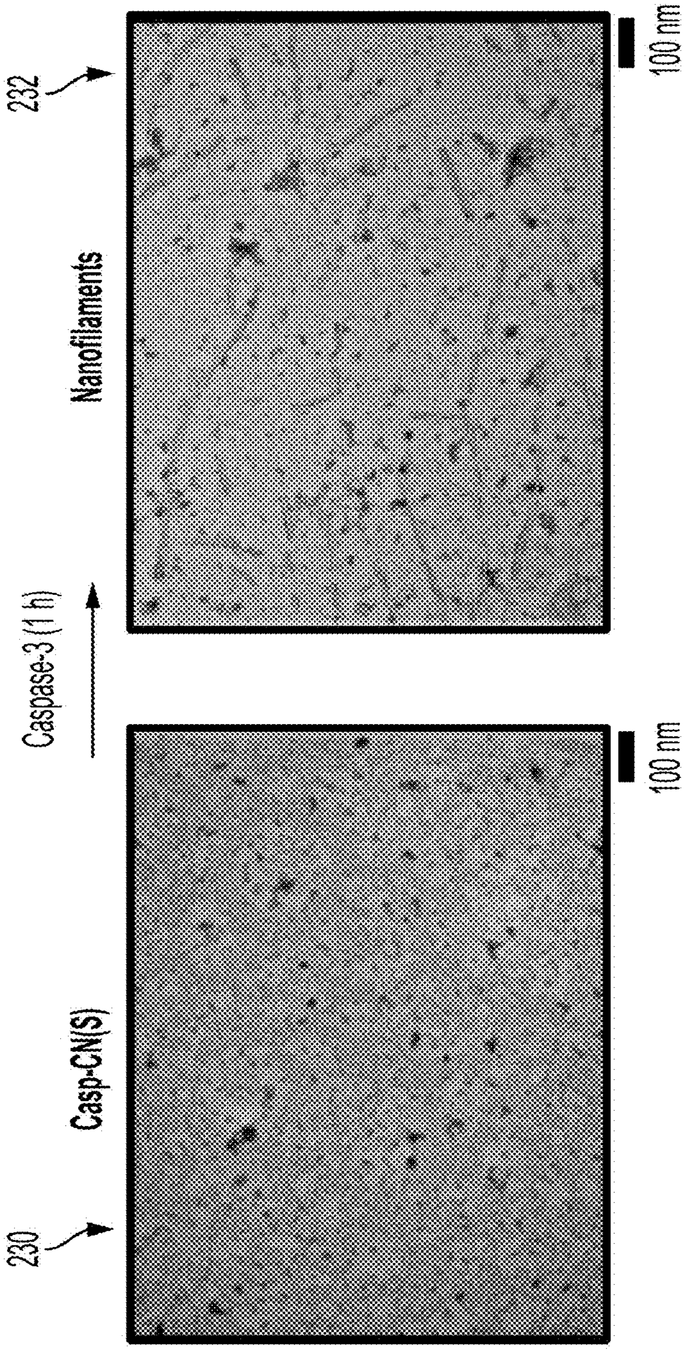
FIG. 2*k* is TEM images of the nano-assemblies formed by Casp-CN(S) before and after the addition of active caspase 3 (25 U/mL, 1 h).
Figure 2L:
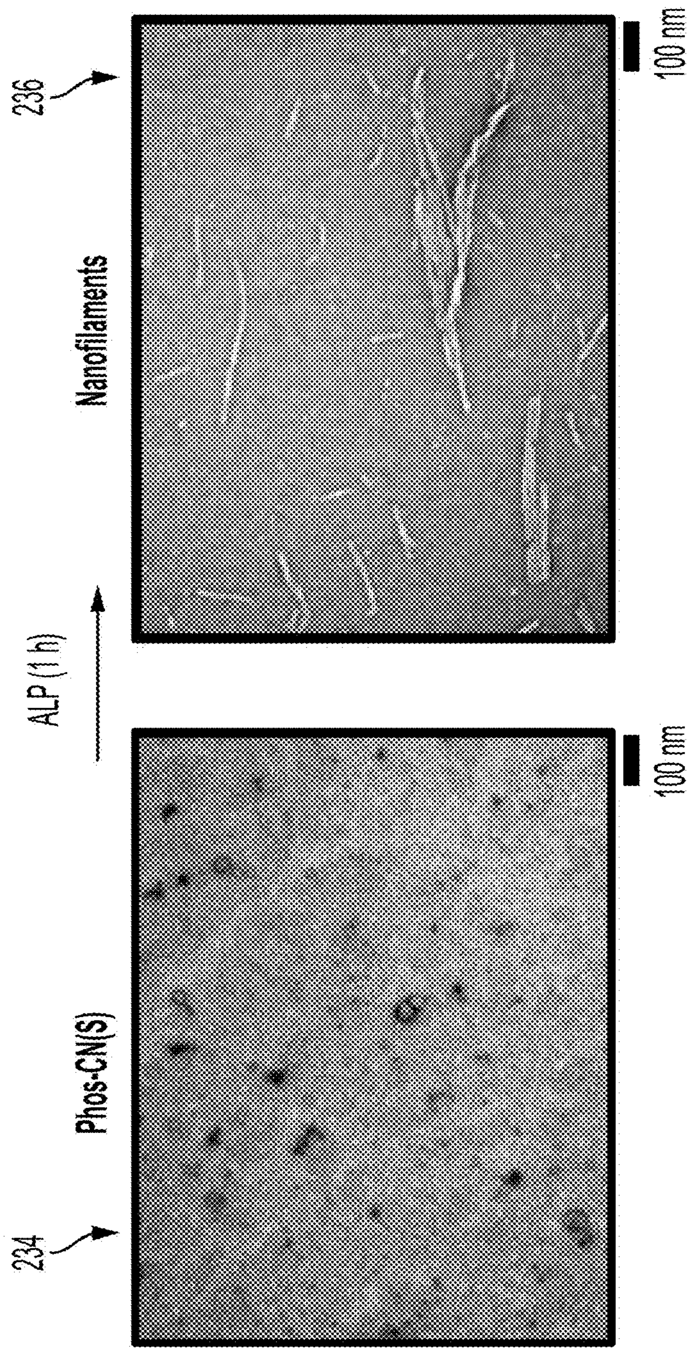
FIG. 2*l* is TEM images of the nano-assemblies formed by Phos-CN(S) before and after the addition of alkaline phosphatase (ALP, 1 U/mL 1 h).
Figure 2N:
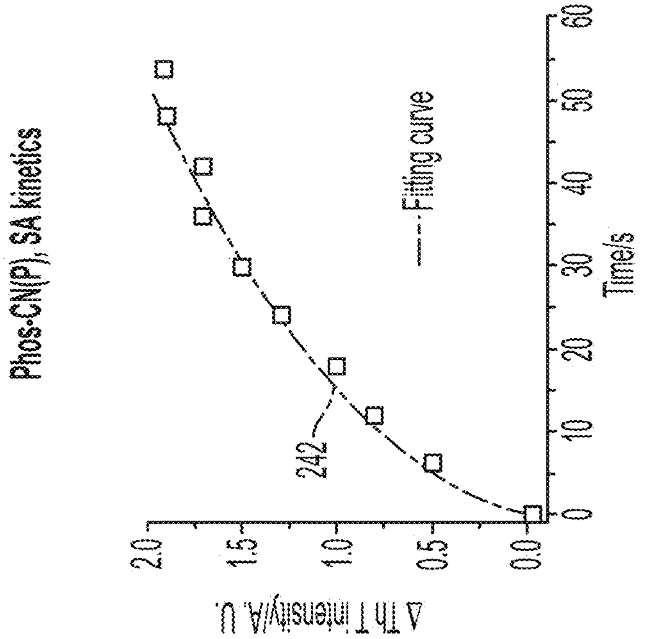
FIGS. 2*m*-2*n* are graphs of self-assembly (SA) kinetics of enzymatic products Casp-CN(P) and Phos-CN(P), respectively.
Figure 2M:
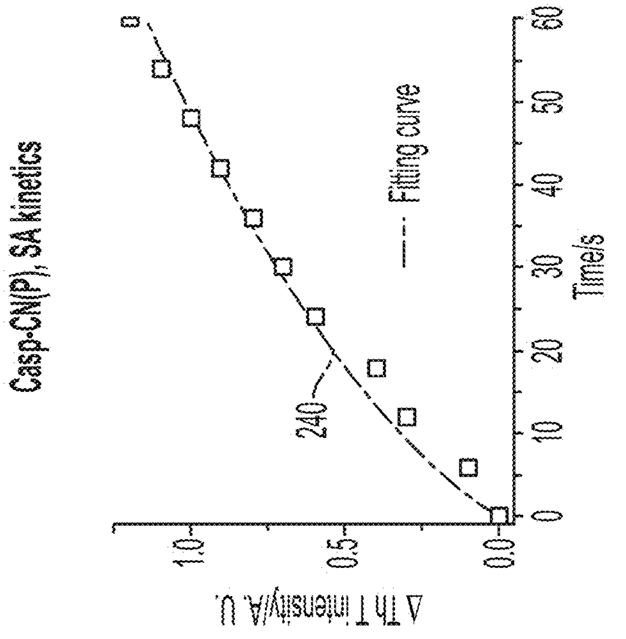

Referring now to FIGS. 2*a-n*, development of nitrile chameleons for mapping specific enzyme activity is now described. FIG. 2*a* shows molecular structures of Casp-CN(S) 202 and the enzymatic product Casp-CN(P) 204. FIG. 2*b* shows molecular structures of Phos-CN(S) 206 and the enzymatic product Phos-CN(P) 208. FIG. 2*c* is a graph of MIP spectra of Casp-CN(S) (210) and the enzymatic product Casp-CN(P) (212), 50 mM in DMSO. FIG. 2*d* is a graph of MIP spectra of Phos-CN(S) (214) and the enzymatic product Phos-CN(P) (216), 50 mM in DMSO. FIGS. 2*e*-2*f* are graphs of MIP signal intensity of Casp-CN(P) (218) and Phos-CN(P) (220), respectively, at different concentration concentrations in DMSO. FIG. 2*g* is a graph showing time-dependent formation of Casp-CN(P) (222) catalyzed by active caspase 3 (25 U/mL). FIG. 2*h* is graph of time-dependent formation of Phos-CN(P) (224) catalyzed by alkaline phosphatase (ALP, 0.5 U/mL). FIGS. 2*i*-2*j* are graphs of UV absorbance changes in the mixtures of Casp-CN(S) (226) and Phos-CN(S) (228) with PBS, ALP, caspase-3 (active), carboxylesterase-1 (CES-1), matrix metalloproteinase-2 (MMP-2), and proteinase K. FIG. 2*k* shows TEM images of the nano-assemblies formed by Casp-CN(S) before (230) and after (232) the addition of active caspase 3 (25 U/mL, 1 h). TEM imaging was repeated independently 3 times with similar results. FIG. 2*l* show TEM images of the nano-assemblies formed by Phos-CN(S) before (234) and after (236) the addition of alkaline phosphatase (ALP, 1 U/mL 1 h). TEM imaging was repeated independently 3 times with similar results. FIGS. 2*m-n* are graphs of self-assembly (SA) kinetics of enzymatic products Casp-CN(P) (240) and Phos-CN(P) (242).

Our system implements nitrile-based enzymatic activity probes. We constructed two probes that selectively map the activity of phosphatase and caspase in living subjects, because both phosphatase and caspase are critical to the survival and death of cells. Our phosphatase probe is generally applicable to different kinds of phosphatase, including alkaline phosphatase (ALP), protein tyrosine phosphatase, acid phosphatase, and other types of phosphatases. The enzyme activity probes are comprised of an enzymatic substrate, a nitrile group (C≡N) as the reporter of enzymatic reaction, and a self-assembly moiety (see FIGS. 2*a*-2*b*). The nitrile-tagged probes for mapping the activity of caspase and phosphatases are named Casp-CN(S) and Phos-CN(S), respectively. The enzymatic products are named Casp-CN (P) and Phos-CN(P), respectively. The enzyme-catalyzed cleavage of the substrates alters the electronic donation from the para-position atoms (N or O), thus, significantly changing the electron density as well as the vibrational frequency of C≡N. Consequently, in the MIP spectra, the C≡N of enzymatic products are spectrally separated from those before enzymatic reactions. The MIP signal intensity of the C≡N of enzymatic products positively correlates with the level of enzyme activity. This reaction-activatable peak shift of C≡N not only reports the occurrence of enzymatic reactions, but also procures the exquisite detection specificity of enzymatic products via bio-orthogonal chemical imaging in the cell-silent region. We further conjugated a self-assembly moiety to the probes to allow in situ ENS for conserving the products at the reaction sites. The ENS of the probes also amplify the imaging contrast via aggregation-enhanced responsiveness (AER), a phenomenon likely caused by concentrating the targeted molecules within the volume of imaging. The amphiphilicity of the probes allows a solubility over 1 mM. We named this category of probes as nitrile chameleons because of the "spectral shift" of C≡N.

As shown in FIG. 2*c*, the MIP spectra of the C≡N bond of Casp-CN(S) 210 and Casp-CN(P) 212 (50 mM, in DMSO) exhibit a sharp peak at 2225 and 2163 $cm^{-1}$, respectively, while in FIG. 2*d* Phos-CN(S) (214) and Phos-CN(P) (216) (50 mM, in DMSO) show narrow-band MIP spectrum of C≡N with a peak at 2215 and 2181 $cm^{-1}$, respectively. These distinctive peaks of C≡N guarantee multi-color MIP imaging of the nitrile probes and the corresponding enzymatic products. Moreover, the MIP signal intensity of the C≡N bond in the enzymatic products is linearly proportional to the concentrations with a limit of detection (LOD) around 5 μM (see graph lines 218, 220 of FIGS. 2*e*-2*f*).

Next, we evaluated the enzymatic conversion efficiency of Casp-CN(S) by caspase-3 (active) (222) and Phos-CN(S) by alkaline phosphatase (ALP) (224) (FIGS. 2*g*-2*h*). Time-course analysis of product formation reveals that the initial speed ($v_0$) is 0.23 $nmol^{-1}$ $min^{-1}$ for Casp-CN(S) by caspase-3, and 0.29 $nmol^{-1}$ $min^{-1}$ for Phos-CN(S) by ALP. The $v_0$ reduces slightly compared with that performed by standard substrates (Ac-DEVD-pNA, 0.33 nmol/min, and P-nitrophenyl phosphate, 0.53 nmol/min) in identical conditions. No reaction occurred in the mixture of Phos-CN(S) or Casp-CN(S) with PBS, carboxylesterase-1 (CES-1), matrix metalloproteinase-2 (MMP-2), and proteinase K (FIGS. 2*i*, 2*j*), confirming the enzyme specificity for the reporters. Transmission electron microscopy (TEM) images of Casp-CN(S) (FIG. 2*k*) and Phos-CN(S) (50 μM, in PBS) (FIG. 2*l*) exhibit sparsely distributed small nanoparticles formed by the self-assembly of the probes. Bulky nanofilaments formed by the self-assembly of products are observed after incubating the probes with corresponding enzymes for 1 hour (232, 236). Thioflavin T (ThT) was employed to examine the kinetics of nanofibril formation by the enzymatic products. As shown in FIGS. 2*m*-2*n*, ThT fluorescence surges within 10 seconds upon mixing with the enzymatic products (10 μM, PBS) (graph lines 240, 242), suggesting a minimal nucleation phase and rapid nanoaggregate formation. Thus, the enzymatic products settle near enzymes due to fast aggregation. Thermodynamically, the chemical potential of nanoaggregate formation positively links to monomer concentration. Therefore, nanofibers predominantly develop near the enzymes because of the maximized product monomer concentration through local generation. However, according to Fick's law of diffusion, the distant product molecules are much less likely to assemble into nanofibers due to reduced concentration. These kinetic and thermodynamic factors ensure the nanoaggregates spatially associate with enzymes, and permits the spatial mapping of enzyme activities.

Figure 3A:
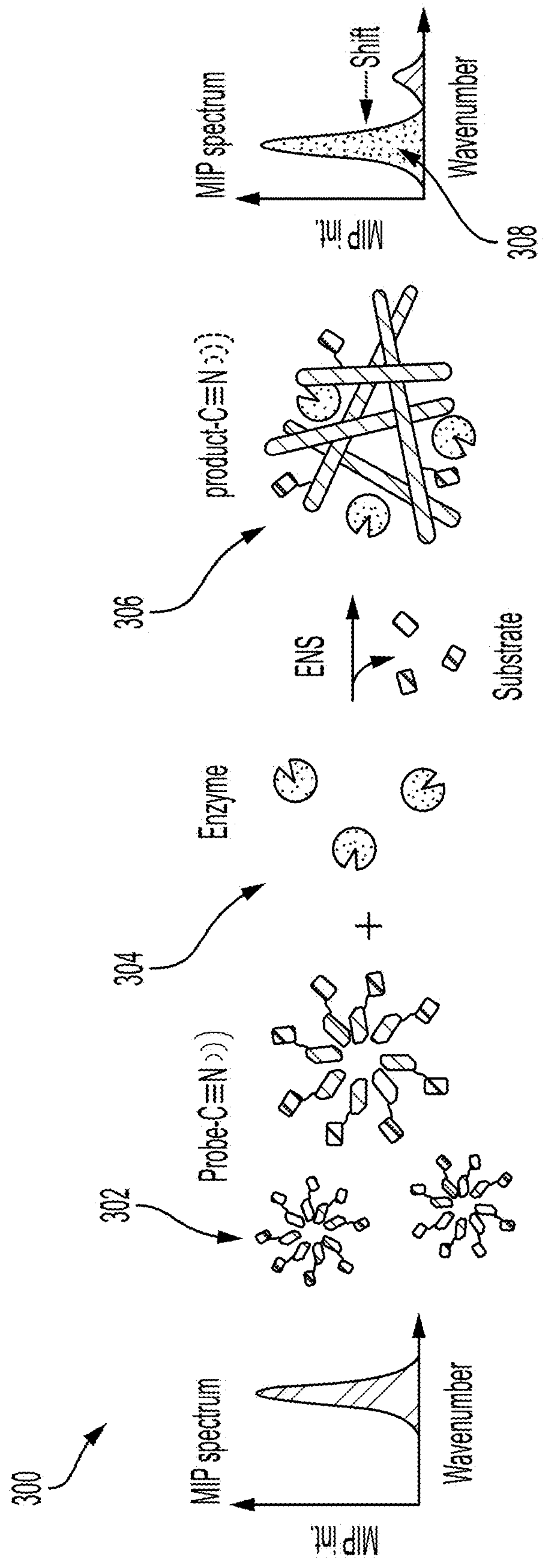
FIG. 3*a* is a schematic illustration of the principle of enzyme activity mapping by real-time MIP imaging of nitrile chameleons.
Figure 3B:
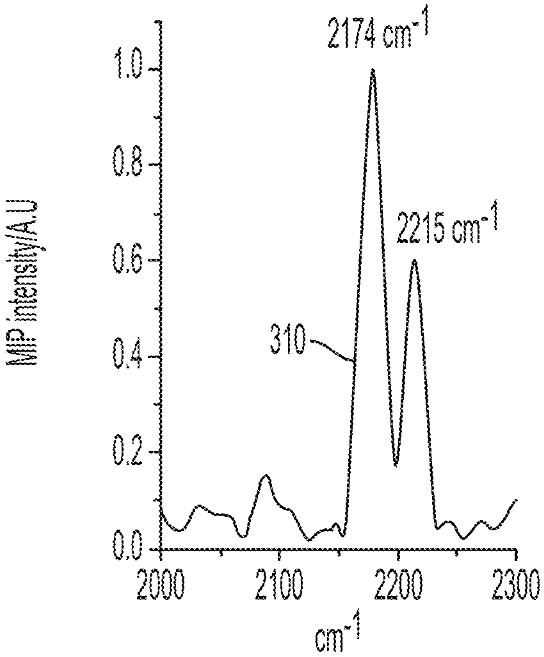
FIG. 3*b* is a graph of pinpointed MIP spectrum from images of FIG. 3*c*.
Figure 3C:
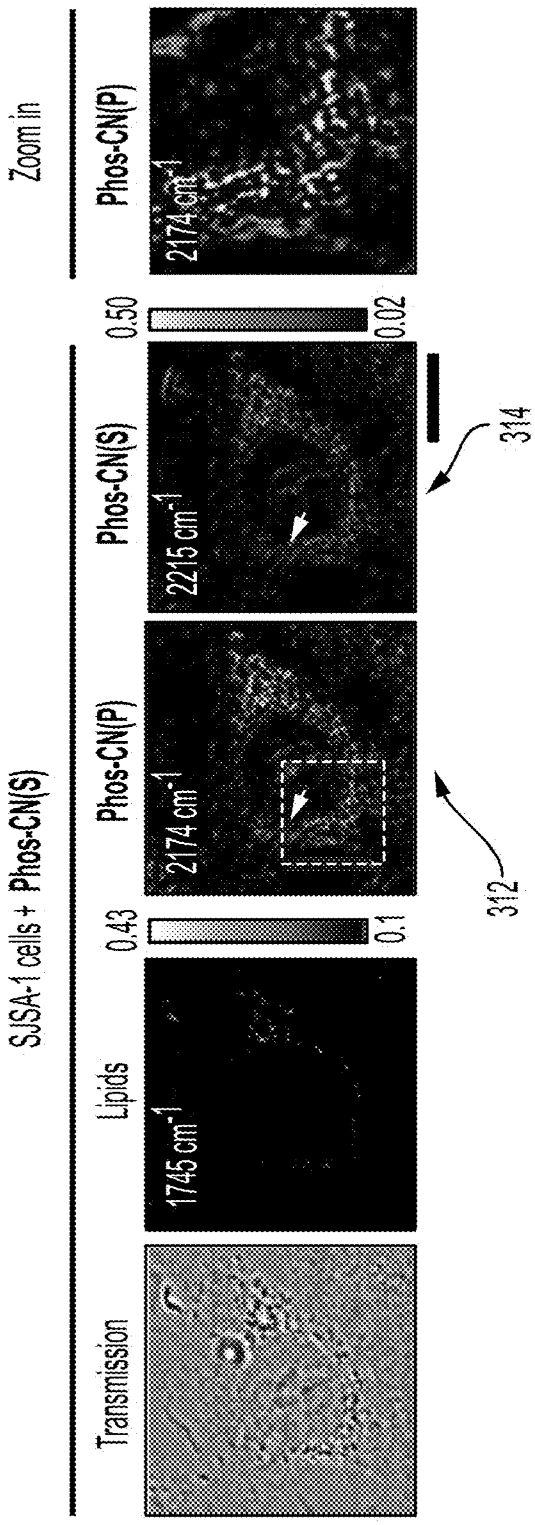
FIG. 3*c* shows MIP images of phosphatase activity profile in living SJSA-1 cells.
Figure 3D:
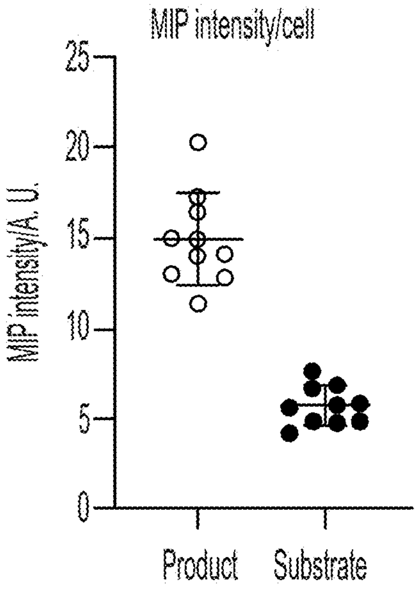
FIG. 3*d* is a graph of quantification of MIP signal intensity of Phos-CN(S) and Phos-CN(P) in cells.
Figure 3E:
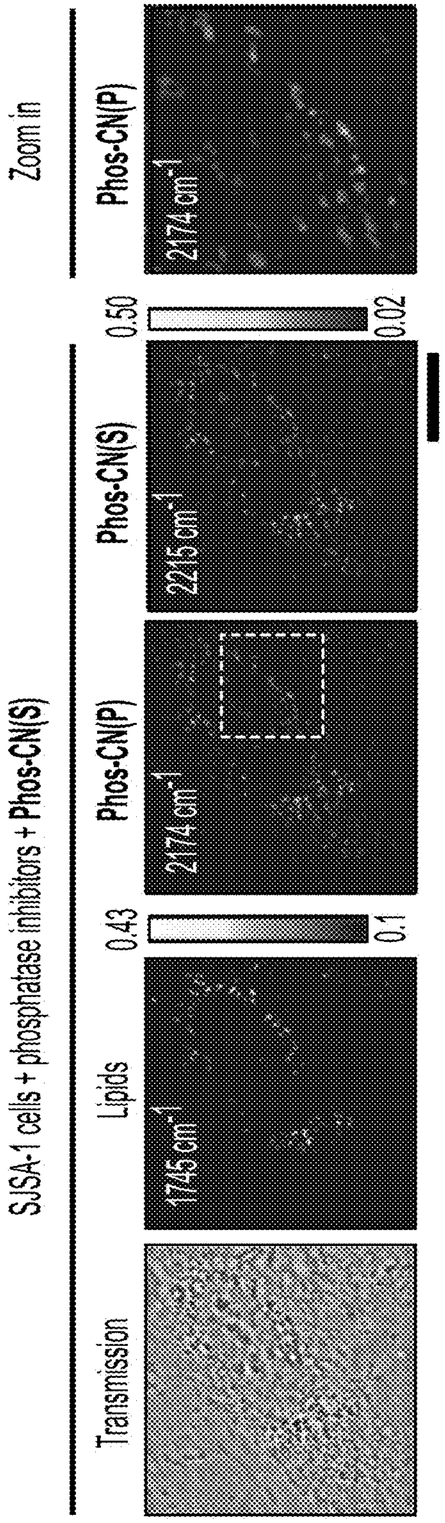
FIG. 3*e* shows MIP images of phosphatase activity profile in phosphatase inhibitor-pretreated SJSA-1 cells.
Figure 3F:
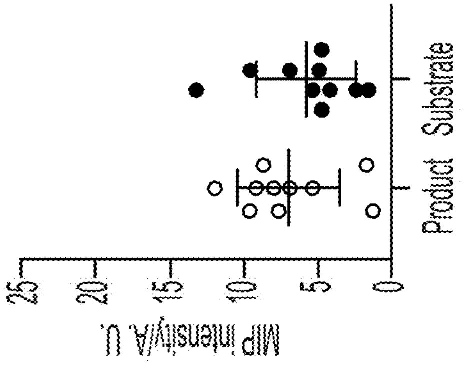
FIG. 3*f* shows quantification of MIP signal intensity of Phos-CN(S) and Phos-CN(P) in phosphatase inhibitor-pretreated SJSA-1 cells.
Figure 3G:
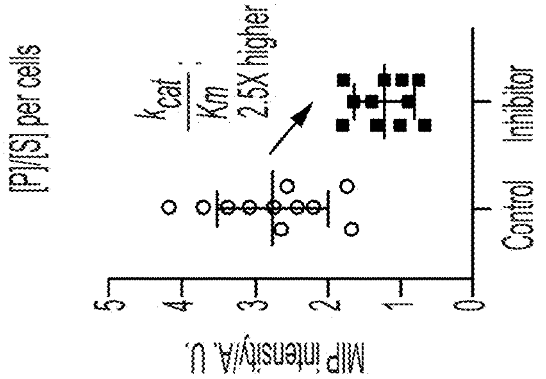
FIG. 3*g* shows quantitation of product-to-substrate ratio ([P]/[S]) in the cells from PIC-pretreated and PIC-free groups.
Figure 3H:
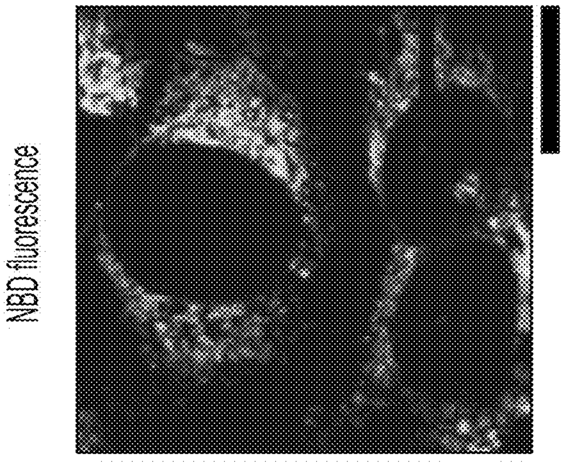
FIG. 3*h* shows confocal fluorescence image of SJSA-1 cells incubated with NBD-label phosphatase activity reporter (NBD-Phos-CN(S), 50 μM, 1 h).
Figure 3I:
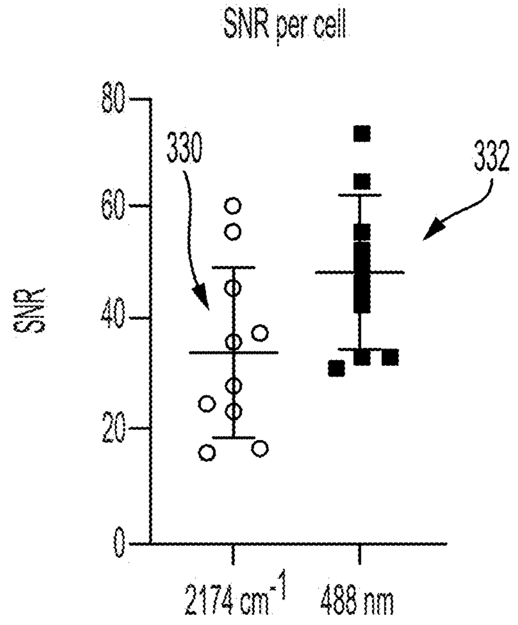
FIG. 3*i* shows a comparison of SNR between MIP imaging of C≡N (at 2174 $cm^{-1}$) and fluorescence imaging of NBD in cancer cells.
Figure 3J:
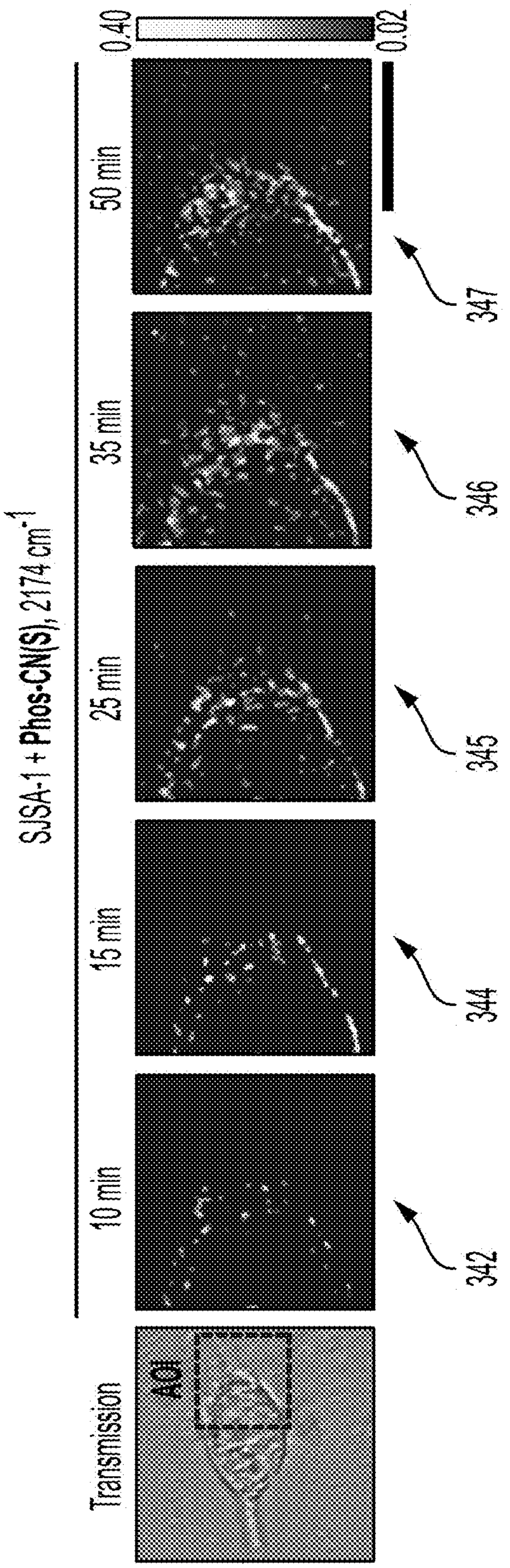
FIG. 3*j* shows time-course MIP images of the phosphatase activity as Phos-CN(S) (50 μM in PBS, room temperature) was added to cells.
Figure 3K:
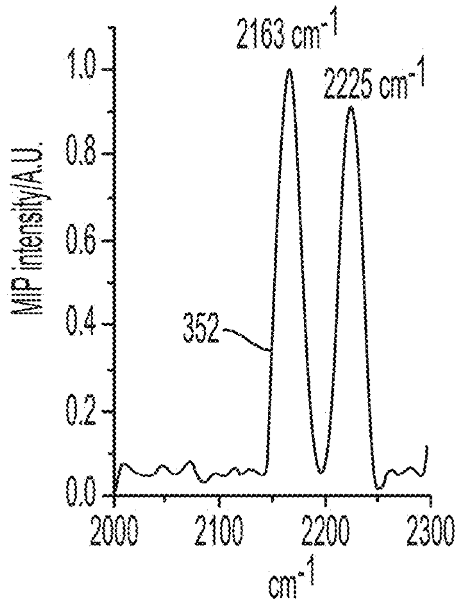
FIG. 3*k* is a graph of pinpoint MIP spectrum, from images of FIG. 3*l*.
Figure 3L:
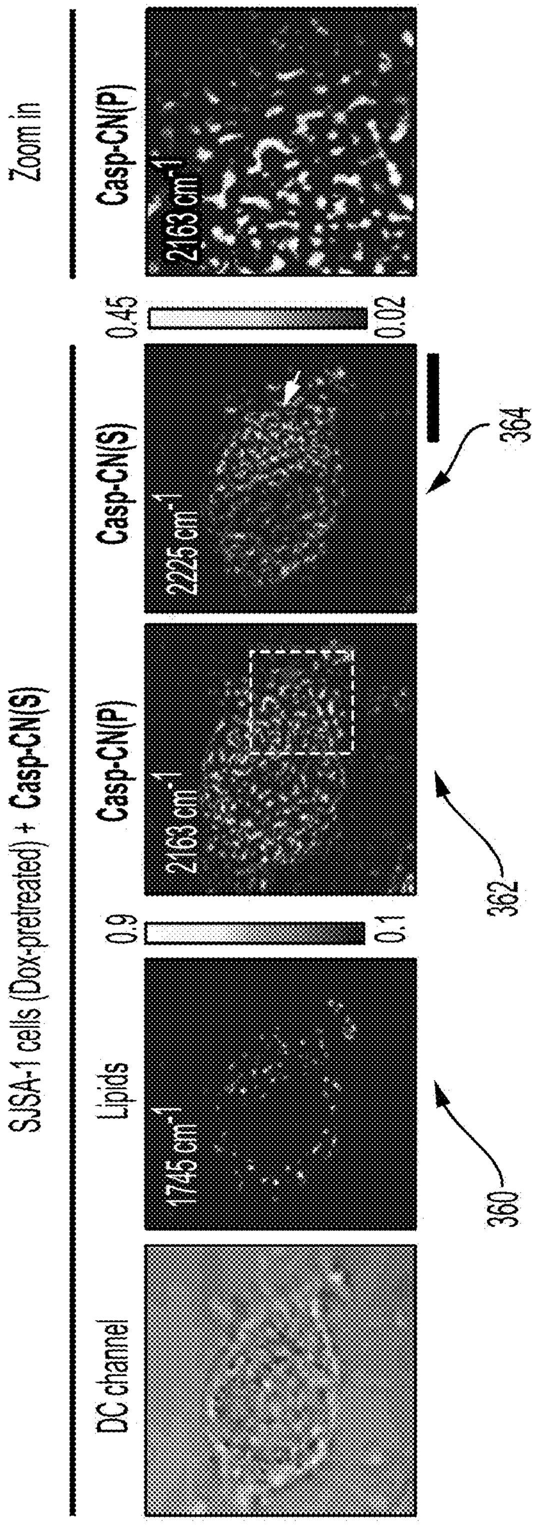
FIG. 3*l* shows MIP images of caspase 3/7 activity profile in Doxorubicin-pretreated SJSA-1 cells.
Figure 3M:
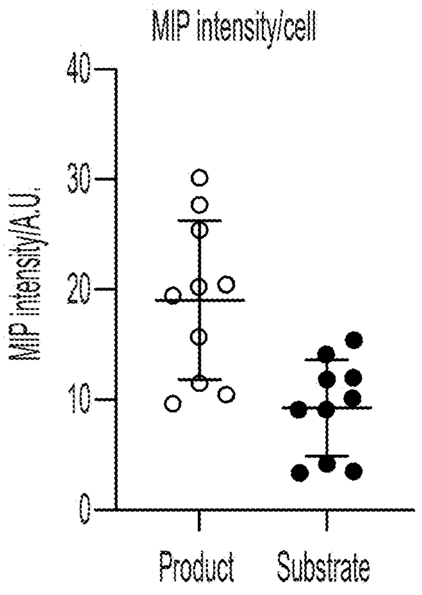
FIG. 3*m* shows quantification of MIP intensity of Casp-CN(S) and Casp-CN(P) in Dox-pretreated cells and the cells from Dox-free control group.

Referring now to FIGS. 3*a*-3*m*, real-time MIP imaging of nitrile chameleons generates the activity maps of caspase 3/7 and phosphatase in living cells. FIG. 3*a* is a schematic illustration 300 of the principle of enzyme activity mapping by real-time MIP imaging of nitrile chameleons. FIG. 3*b* is a graph of pinpointed MIP spectrum 310, indicated by the arrows in images 312, 314 of FIG. 3*c*. FIG. 3*c* shows MIP images of phosphatase activity profile in living SJSA-1 cells (Scale bar=30 μm). FIG. 3*d* is a graph of quantification of MIP signal intensity of Phos-CN(S) and Phos-CN(P) in cells (n=10 cells, data are presented as mean±SD). FIG. 3*e* shows MIP images of phosphatase activity profile in phosphatase inhibitor-pretreated SJSA-1 cells (Scale bar=30 μm). FIG. 3*f* shows quantification of MIP signal intensity of Phos-CN(S) and Phos-CN(P) in phosphatase inhibitor-pretreated SJSA-1 cells (n=10 cells, data are presented as mean±SD). FIG. 3*g* shows quantitation of product-to-substrate ratio ([P]/[S]) in the cells from PIC-pretreated and PIC-free groups (n=11 cells, data are presented as mean±SD). FIG. 3*h* shows confocal fluorescence image of SJSA-1 cells incubated with NBD-label phosphatase activity reporter (NBD-Phos-CN(S), 50 μM, 1 h) (scale bar=30 μm). FIG. 3*i* shows a comparison of SNR between MIP imaging of C≡N (at 2174 $cm^{-1}$) (330) and fluorescence imaging of NBD in cancer cells (332). Each dot on hta graph represents a cell (n=10 cells, data are presented as mean±SD). FIG. 3*j* shows time-course MIP images of the phosphatase activity as Phos-CN(S) (50 μM in PBS, room temperature) was added to cells (scale bar=30 μm). FIG. 3*k* is a graph of pinpoint MIP spectrum 350, indicated by arrows in images 362, 364 of FIG. 3*l*. FIG. 3*l* shows MIP images of caspase 3/7 activity profile in Doxorubicin-pretreated SJSA-1 cells. (scale bar=30 μm). FIG. 3*m* shows quantification of MIP intensity of Casp-CN(S) and Casp-CN(P) in Dox-pretreated cells and the cells from Dox-free control group (n=10 cells, data are presented as mean±SD).

Real-time MIP imaging of enzyme activities in living cells was conducted. As shown in FIG. 3*a*, the probes 302 enter the cells and react with the corresponding enzymes 304, generating products 306 that exhibit MIP signal 308 at new wavenumbers. The MIP signal intensity 308 from products 306 is correlated with enzyme activity. The ENS of probes produce non-diffusive nanofilaments which uncover the reaction sites and enhance the imaging contrast by AER. We first used this approach to map the activity of phosphatase in SJSA-1 cells, an osteosarcoma cell line with high phosphatase expression. A working concentration of 50 μM was chosen based on cytotoxicity assay. All MIP images in the cell-silent window undergo a subtraction of water background unless specially mentioned. After the treatment of Phos-CN(S) (1 h), a pinpointed MIP spectrum 310 (FIG. 3*b*) in the silent window inside a cell exhibits a sharp peak at 2174 $cm^{-1}$ arising from the C≡N of the dephosphorylated products (Phos-CN(P)), and a smaller peak at 2215 $cm^{-1}$ originating from the C≡N of Phos-CN(S). This MIP spectrum identifies the optimal wavenumbers for imaging and validates the intracellular chemical components. The peaks of the C≡N inside cells shift compared to that in DMSO (FIG. 2*d*), probably due to the Stark effect. Live-cell MIP imaging at 1745 $cm^{-1}$ reveals the profiles of lipid droplets in SJSA-1 cells, as shown in FIG. 3*c*. Subsequent MIP images of the same cells at 2174 $cm^{-1}$ show strong signal from Phos-CN(P), while the intracellular MIP signal from Phos-CN(S) at 2215 $cm^{-1}$ is weaker (FIG. 3*d*). These results suggest an efficient cellular uptake of the phosphatase activity probe, and that the phosphatases in SJSA-1 cells substantially convert Phos-CN(S) to Phos-CN(P), disclosing a robust intracellular phosphatase activity.

Instead of a diffusive distribution, Phos-CN(P) exposes intricate subcellular structures varied by MIP intensity in the mapping (FIG. 3*c*), indicating a heterogeneous biodistribution of phosphatase activity. To verify the non-diffusive property of nanofilaments in cells, we incubated cancer cells with Phos-CN(S) (1 hour) followed by fixation. We then sequentially captured two MIP images within the same field of view at a one-hour interval. The results show that little movement occurred during the one-hour interval, suggesting that the nanofilaments are highly immobile within cells. Although the Stokes-Einstein equation suggests high mobility for 100-nm particles in water, the nanofilaments formed by enzymatic products exhibited non-diffusive behaviors in the cells, likely due to the intertwining of nanofilaments, which constructs rigid nanonetworks that interact with cellular structures, thus restricting the mobility within the cellular environment. Such immobility ensures the spatial accuracy of enzyme activity mapping. However, the dissolved portion of Phos-CN(S) is hardly visible due to the lack of AER. Integrated MIP and widefield fluorescence imaging validate a good colocalization (Pearson's r=0.7) between the MIP signal from Phos-CN(P) and the immunofluorescence from phosphatase antibodies (e.g., Anti-ALP), confirming the high spatial accuracy of mapping. As controls, we hardly observed MIP contrast in the cells without Phos-CN(S) treatment at 2174 $cm^{-1}$. These results collectively confirm successful mapping of phosphatase activity in living SJSA-1 cells by real-time MIP imaging of the nitrile chameleon.

Phosphatase inhibitor cocktails (PIC)-pretreated SJSA-1 cells incubated with Phos-CN(S) show a punctate distribution of Phos-CN(P) and Phos-CN(S) with much weaker MIP signals (FIGS. 3*e* and 3*f*) compared to the cells from inhibitor-free group (FIGS. 3*c* and 3*d*), which agrees with the phosphatase activity inhibition. These results validate that Phos-CN(S) can spatiotemporally unveil phosphatase activity change in cells. Given that the phosphatase level (e.g., ALP) in cells remains unchanged after PIC treatment, the relative enzyme catalytic efficiency ($k_{cat}/K_M$) of phosphatase between the cells from PIC-pretreated and inhibitor-free groups can be approximately determined by the product-to-substrate ratio ([P]/[S], determined by the ratio of intracellular MIP intensity at 2174 $cm^{-1}$ versus 2215 $cm^{-1}$) in cells. The extent of PIC-induced inhibition on the $k_{cat}/K_M$ of phosphatase in cells can be evaluated by this relative value. Statistically, the average [P]/[S] in PIC-pretreated cells is 2.5 times lower than the one in PIC-free group (FIG. 3*g*), indicating that the average $k_{cat}/K_M$ of the phosphatase in SJSA-1 cells decreases 60% through PIC treatment.

While the LOD of enzymatic products in DMSO approximate 5 μM, the minimum detectable concentration of the same molecules in cells, upon nanofilaments formation, is estimated to be around 600 nM. Due to the uneven distribution of nanoaggregates in water, we used hyperspectral MIP images of Phos-CN(P) suspensions at concentration as low as 800 nM in PBS to substantiate this calculation. The peak of nitrile group is discernable in the spectrum obtained from the hyperspectral images, affirming the sub-micromolar sensitivity of MIP in detecting the nanoassemblies of enzymatic products. To further validate the high sensitivity of MIP imaging, we compared the MIP images to the fluorescence images of cells incubated NBD-Phos-CN(S), a nitrobenzofurazan (NBD)-tagged Phos-CN(S). Statistically, MIP images of C≡N at 2174 $cm^{-1}$ and fluorescence images of NBD (FIG. 3*h*) of the cancer cells incubated with NBD-Phos-CN(S) (50 μM, 1*h*) showed comparable signal to noise ratio (SNR) (FIG. 3*i*). Here, SNR is the mean signal intensity in cells divided by that of blank area. Since C≡N and NBD exist in the molecule in a 1:1 ratio, this result indicates that the detection ability of C≡N by MIP resembles to that of NBD by fluorescence in cells. Furthermore, MIP imaging outperforms fluorescence imaging by a photobleaching-free property, making it more suitable for observing continuous events in living systems.

Considering the high sensitivity and resistance to photobleaching, we conducted real-time monitoring of dephosphorylation reaction in cells by MIP imaging as Phos-CN(S) is introduced to the cells. As shown in FIG. 3*j*, within 10 minutes of Phos-CN(S) addition (image 342), distinct puncta of dephosphorylated products were observed, indicating an efficient endocytosis-dependent cell entry and early endosomal dephosphorylation. Between 15 to 50 minutes (images 344, 345, 346, 347), the MIP signal of enzymatic products appeared in other cellular regions with crooked-stripe patterns, indicating that Phos-CN(S) escaped from the endosomes and underwent dephosphorylation by the phosphatases in various cellular locations. The Nanoparticles formed by the amphiphilic nitrile chameleons may escape from endosomes through endosomal membrane disruption or perforation. The variation in phosphatase activity patterns at different time points is attributed to the dynamic movements of cellular structures within live cells. As previously discussed, the nanofilaments intertwine with cellular structures, causing the nanofilaments to move along with these structures. Furthermore, we utilized NBD-Phos-CN(S) to study the cellular uptake mechanism of nitrile chameleons because NBD fluorescence cannot distinguish between substrate and product. NBD fluorescence inside the cells was significantly reduced by ATP synthetase inhibitor (oligomycin, 5 μM), suggesting that the internalization of the probes occur through endocytosis.

Other than phosphatase, we profiled caspase-3/7 activity in live cancer cells. Doxorubicin (Dox) efficiently induces apoptosis in SJSA-1 cells for activating caspase-3/7. After the incubation with Casp-CN(S) (50 μM, 1 h), a pinpointed MIP spectrum inside a cell exhibits a sharp peak at 2163 $cm^{-1}$ arising from the C≡N in Casp-CN(P) and a smaller peak originating from the C≡N in Casp-CN(S) at 2225 $cm^{-1}$ (FIG. 3*k*). This MIP spectrum provides the optimal wavenumbers for imaging and validates the intracellular chemical compositions. MIP imaging at 1745 $cm^{-1}$ generates the map of lipid droplets in the cells (image 360, FIG. 3*l*). MIP images of the Dox-pretreated SJSA-1 cells show intensive MIP signal from Casp-CN(P) at 2163 $cm^{-1}$ (362) and less signal from Casp-CN(S) at 2225 $cm^{-1}$ (364) with detailed spatial information (FIGS. 3*l* and 3*m*). These results indicate an efficient internalization of the caspase activity probe into cells, and a high caspase-3/7 activity in the Dox-pretreated SJSA-1 cells. Colocalization between Phos-CN(S) (FIG. 3*c*, 312) and Phos-CN(P) (314), as well as Casp-CN(S) (FIG. 3*l*, 364) and Casp-CN(P) (362) is observed, suggesting the coassembly between probes and products into non-diffusive nanofilaments during ENS. Tandem MIP and widefield fluorescence imaging validated a high spatial correlation between the MIP signal from Casp-CN(P) and the immunofluorescence from Caspase-3 (active) antibody (Pearson's r=0.72). These results confirm a precise mapping of caspase-3/7 activity in apoptotic cells. While the nitrile chameleons are noncytotoxic, incubating cancer cells with Casp-CN(S) showed a weak but non-zero MIP signal from Casp-CN(P). Such signal disappeared upon the pretreatment of caspase-3/7 inhibitors. Together, these results indicate the presence of low-levels caspase-3/7 activity in non-apoptotic cells.

The hydrophobic enzymatic products show little interaction with the plasma membrane or the lipid droplets (FIGS. 3*c* and 3*l*). The overall MIP intensity of C≡N increases along with the enzymatic cleavage in the cells (FIG. 3*c*-*f*, 3*l*), despite the same import efficiency of probe molecules into different the cell populations. This phenomenon can be explained by the assembly of products and substrates into non-diffusive nanofilaments after enzymatic cleavage, leading to an improved imaging detectability and cellular retention of C≡N. The increased detectability arises from a higher molecular density in the imaging volume, enabling the targeted signals to stand out from background noise. Consequently, nanofiber formation corresponds to elevated C≡N accumulation and imaging detectability within cells, leading to higher MIP signal intensity. Incubating cancer cells with the control probes that are resistant to caspase-3/7 and phosphatase exhibited negligible MIP signal in cells at the wavenumber of the enzymatic products, supporting the accurate enzyme activity detection by MIP imaging of nitrile chameleons.

Figure 4A:
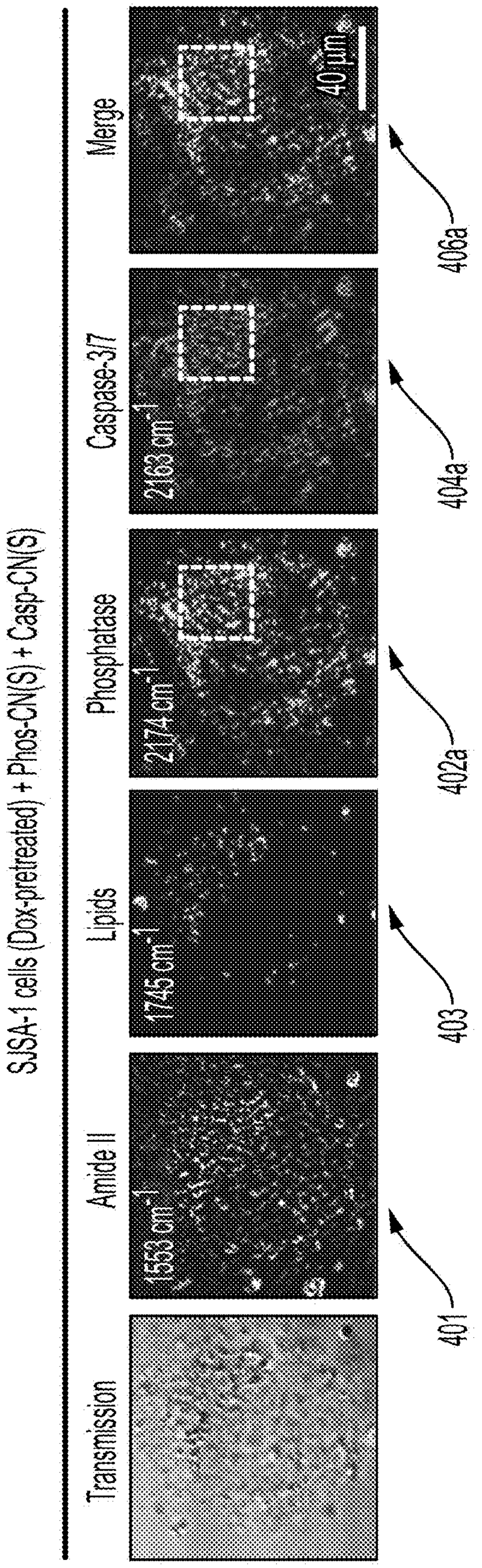
FIG. 4*a* shows images of simultaneous visualization of phosphatase and caspase-3/7 activity profile in Dox-pretreated SJSA-1 cells.
Figure 4B:
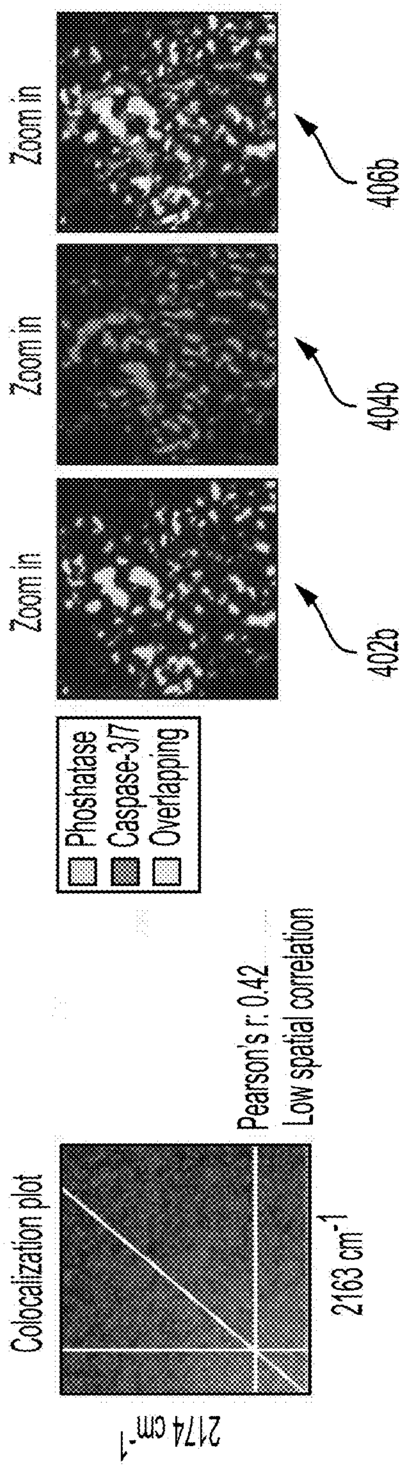
FIG. 4*b* shows colocalization analysis of the mapping in the images of FIG. 4*a*.
Figure 4C:
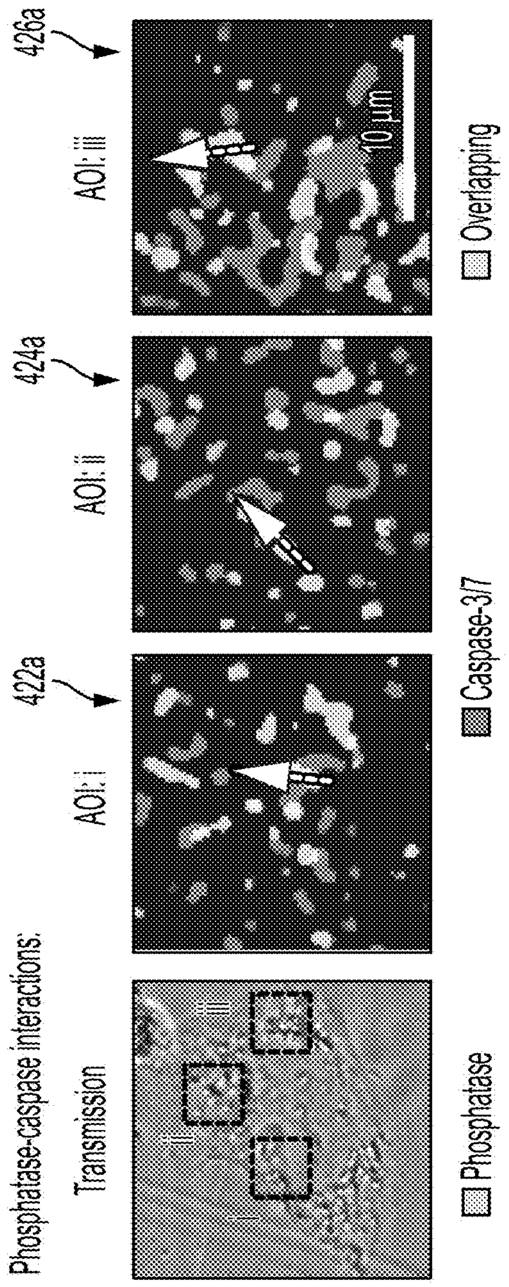
FIG. 4*c* shows spatial interaction between phosphatase and caspase-3/7 in Dox-pretreated SJSA-1 cells.
Figure 4D:
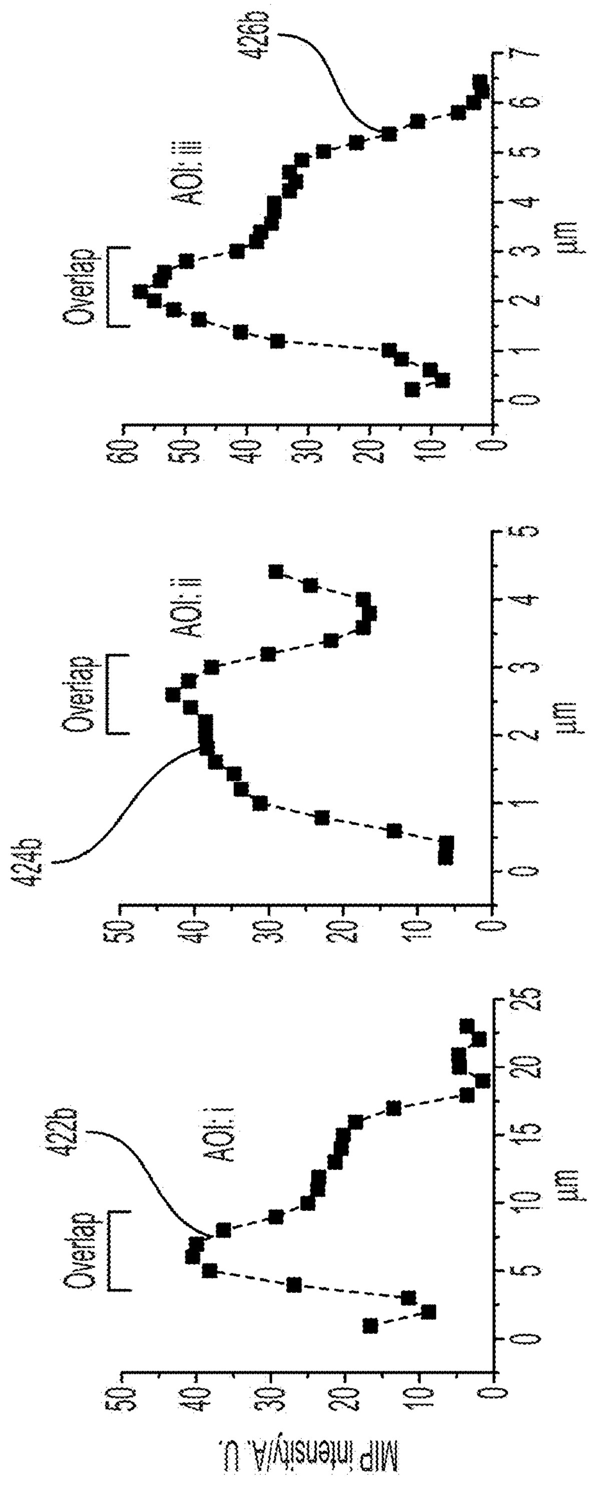
FIG. 4*d* shows intensity plots of Phos-CN(P) along the arrows shown in the images of FIG. 4*c*.
Figure 4F:
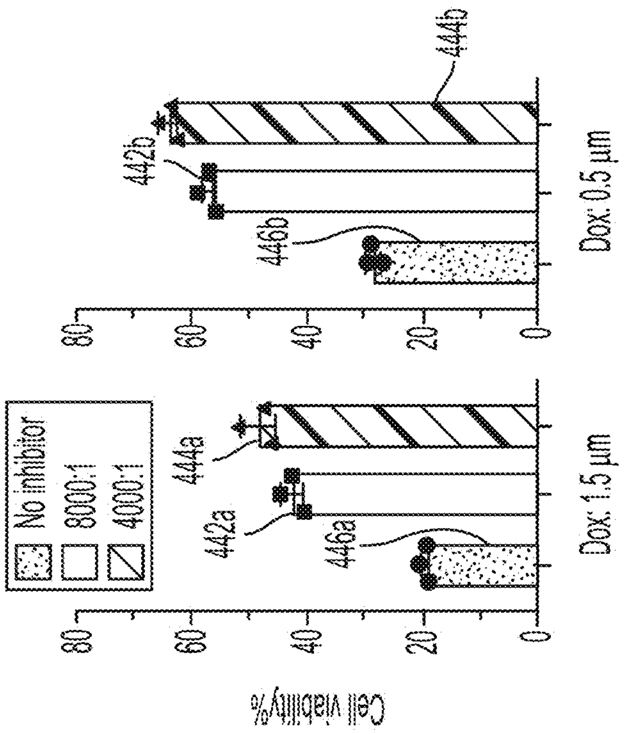
FIG. 4*f* shows cell viability assays of SJSA-1 cells incubated with Dox in the presence and absence of phosphatase inhibitor cocktails.
Figure 4E:
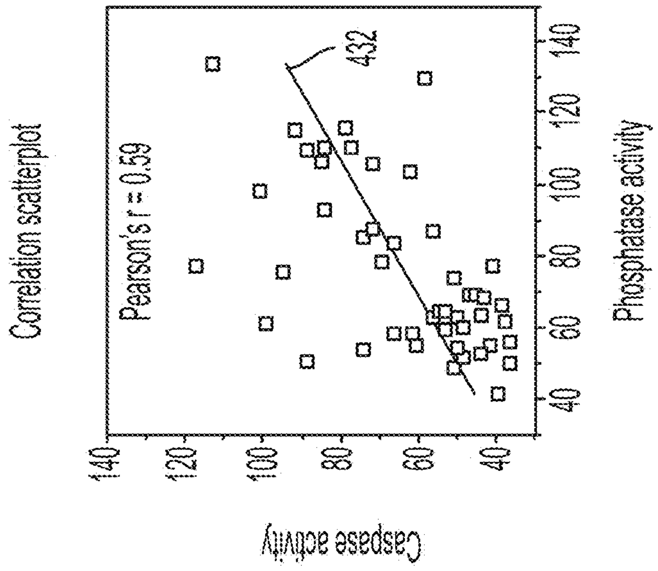
FIG. 4*e* shows a correlation scatterplot of caspase-3/7 and phosphatase activity in Dox-pretreated SJSA-1 cells.

Referring now to FIGS. 4*a*-4*f*, MIP imaging of nitrile chameleons in live cancer cells provides evidence of caspase-phosphatase cooperation in apoptosis. FIG. 4*a* shows simultaneous visualization of phosphatase and caspase-3/7 activity profile in Dox-pretreated SJSA-1 cells. This experiment was repeated independently 12 times with similar results. FIG. 4*b* shows colocalization analysis of the mapping in the images of FIG. 4*a*, with images 402*a*, 404*a*, 406*a*, corresponding to images 402*b*, 404*b*, 406*b*, respectively. FIG. 4*c* shows spatial interaction between phosphatase and caspase-3/7 in Dox-pretreated SJSA-1 cells. Similar results were observed in 12 independent experiments. FIG. 4*d* shows intensity plots, represented by graph lines (422*b*, 424*b*, 426*b*) of Phos-CN(P) along the arrows of images 422*a*, 424*a*, 426*a*, respectively, of FIG. 4*c*. FIG. 4*e* shows a correlation scatterplot of caspase-3/7 and phosphatase activity in Dox-pretreated SJSA-1 cells (with fit line 432). FIG. 4*f* shows cell viability assays of SJSA-1 cells incubated with Dox in the presence and absence of phosphatase inhibitor cocktails. Phosphatase inhibitor cocktails were diluted by 4000 (graph lines 442*a*, 442*b*) and 8000 times (graph lines 444*a*, 444*b*), respectively, using culture medium (n=3 independent experiments, data are presented as mean±SD) (no inhibitor shown by graph lines 446*a*, 446*b*).

MIP imaging reveals caspase-phosphatase interaction. The MIP spectra of C≡N in Phos-CN(P) and Casp-CN(P) in cells appear as narrow bands at unique wavenumbers (see FIGS. 3*b* and 3*k*), enabling multispectral imaging of these two enzymatic products. Thus, we simultaneously disclosed the activity distribution of phosphatase and caspase-3/7 in apoptotic cancer cells by MIP imaging of Phos-CN(P) and Casp-CN(P), because the yield of enzymatic products aligns with the level and biodistribution of enzyme activities. As shown in FIG. 4*a*, MIP imaging at 1553 $cm^{-1}$ (image 401, amide II) and 1745 $cm^{-1}$ (image 403) displays the location and morphology of proteins and lipid droplets, respectively, in the Dox-pretreated SJSA-1 cells. After incubating the apoptotic cells with Phos-CN(S) and Casp-CN(S), strong MIP signals from the C≡N of Phos-CN(P) and Casp-CN(P) with fine textures are observed in cells (FIG. 4*a*), suggesting a high-level activity of phosphatase (402*b*) and caspase-3/7 (404*b*) in the cells. The merge channel and colocalization analysis confirms a weak spatial correlation between the MIP signals from Phos-CN(P) and Casp-CN(P) (Pearson's r=0.42, FIG. 4*b*), validating that MIP imaging of nitrile chameleons not only visualizes, but also spatially and spectrally distinguishes the activity distribution of different enzymes.

Interestingly, while the activity maps of phosphatase and caspase-3/7 are mostly independent, sporadic coexistences were observed in the cells (FIG. 4*c*). The overlapping between the activity maps of phosphatase and caspase-3/7, while infrequent, suggests the coexistence and co-assembly of their enzymatic products in certain areas within the cells. Since the MIP signal of enzymatic products spatially corresponds to the biodistribution of enzyme activities, such overlapping indicates that the activity of caspase-3/7 and phosphatase are spatially close in some areas of the cells, suggesting potential phosphatase-caspase interactions in apoptosis. It is reported that PTEN and PTP-PEST are potential substrates of caspase-3. Importantly, the caspase-3-catalyzed cleavage of PTP-PEST increases the catalytic activity of PTP-PEST. Notably, in the activity map of phosphatase and caspase-3/7, areas with colocalization generally exhibit stronger MIP signal from Phos-CN(P) than the ambient, as revealed by the intensity plots (422*b*, 424*b*, 426*b* of FIG. 4*c*) along the arrows of images 422*a*, 424*a*, 426*a*, respectively, of FIG. 4*c*. This indicates a higher phosphatase activity in the sites that are coupled with caspase 3/7 activity. Statistically, the activity level of phosphatase in SJSA-1 cell population positively associated with that of caspase-3/7, as indicated by graph line 432 in FIG. 4*e*. These results indicate potential caspase-phosphatase interactions during apoptosis, probably through enzymatic cleavage with some phosphatase as the substrates of caspase. Such interactions appear to influence the activity of phosphatases in cells. Nevertheless, it's important to note that the alterations in phosphatase activity during apoptosis may occur through many other biochemical processes within the apoptosis signaling pathway, rather than being solely attributed to the direct processing of phosphatases by caspase-3/7.

To further confirm the interaction between phosphatase and caspase-3/7 during apoptosis, we imaged the intracellular distribution of caspase-3 proteins (full-length and cleaved) and the activity map of phosphatase in Dox-pretreated cancer cells in the presence and absence of a caspase-3 inhibitor (Z-DEVD-FMK, 10 μM). In this study, caspase-3 protein in the cancer cells was visualized by immunofluorescence staining using a confocal fluorescence microscope. To locate the phosphatase activity alongside caspase-3 protein via confocal fluorescence microscopy, we incubated cancer cells with NBD-Phos-CN(S) and located phosphatase activity through NBD fluorescence. This approach, known as fluorescence ENS, has been widely used to expose the location of enzyme activity. The results demonstrated that cancer cells in the caspase inhibitor-treated group exhibited a significantly reduced spatial overlapping frequency between the phosphatase activity map and the caspase-3 proteins than the cells in the inhibitor-free group. This supports our hypothesis that caspase-3 and some phosphatases interact in the colocalized regions through enzymatic cleavage, with some phosphatase acting as the substrate of caspase-3. Thus, the simultaneous mapping of phosphatase and caspase-3/7 activity probably localizes the caspase-mediated cleavage of phosphatase, likely PTP-PEST, in the apoptotic SJSA-1 cells. In addition to SJSA-1, we observed a similar scenario in MIA PaCa-2. Furthermore, a slight inhibition of phosphatase activity rescued cancer cells from Dox-induced cell death (FIG. 4*f*), strengthening the notion that phosphatase activity is crucial in apoptosis signaling.

Figure 5B:
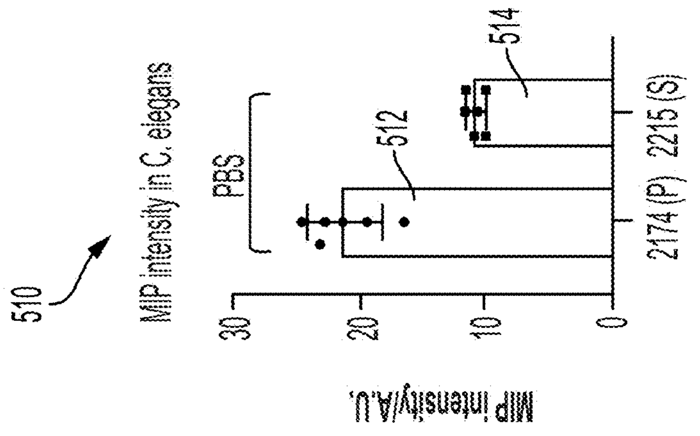
FIG. 5*b* is a graph showing quantification of the MIP signal intensity from Phos-CN-(P) and Phos-CN-(S) in the inhibitor-free *C. elegans.*
Figure 5A:
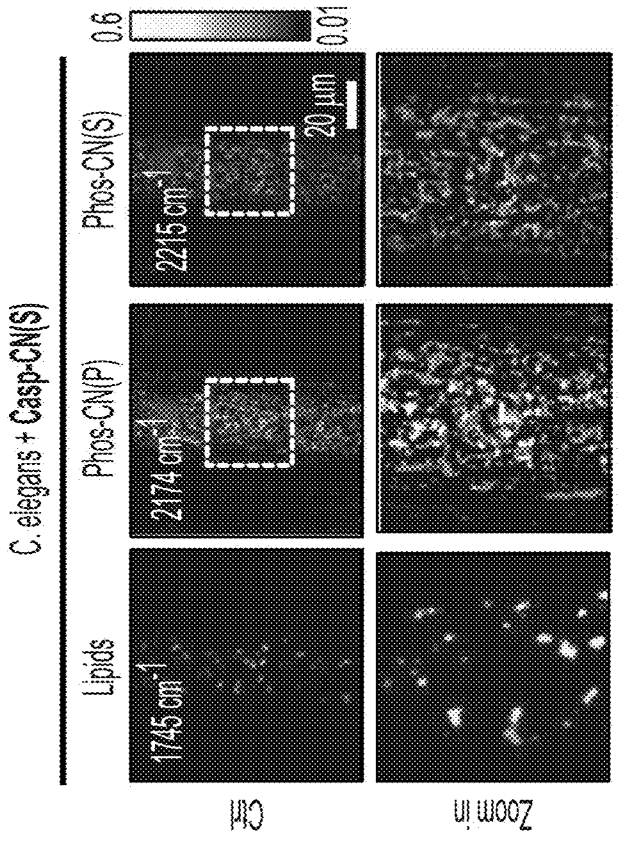
FIG. 5*a* shows MIP imaging of phosphatase profile in living *C. elegans.*
Figure 5D:
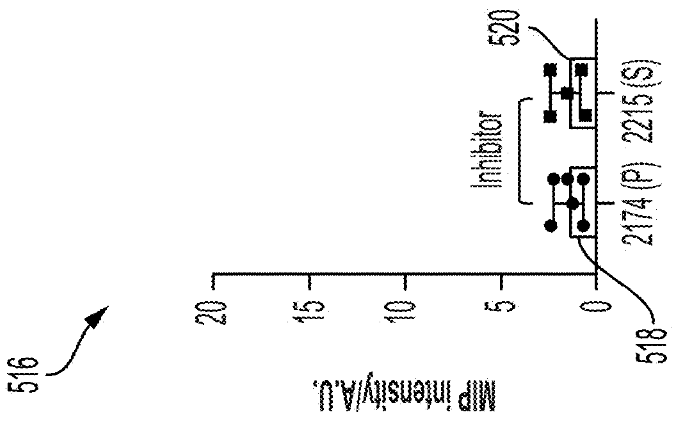
FIG. 5*d* is a graph showing quantification of the MIP signal intensity from Phos-CN-(P) and Phos-CN-(S) in the PIC-pretreated *C. elegans.*
Figure 5C:
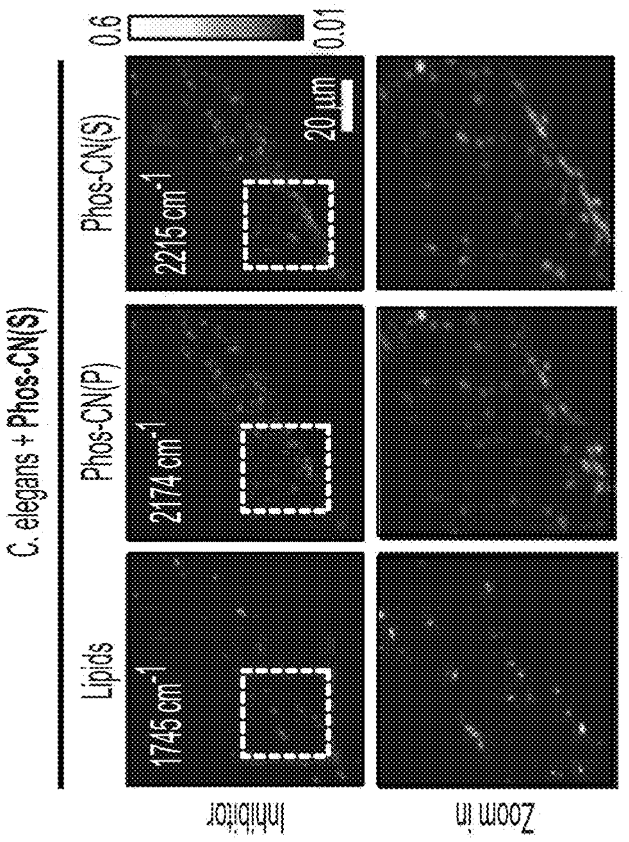
FIG. 5*c* shows MIP imaging of phosphatase activity profile in the PIC-pretreated *C. elegans.*
Figure 5G:
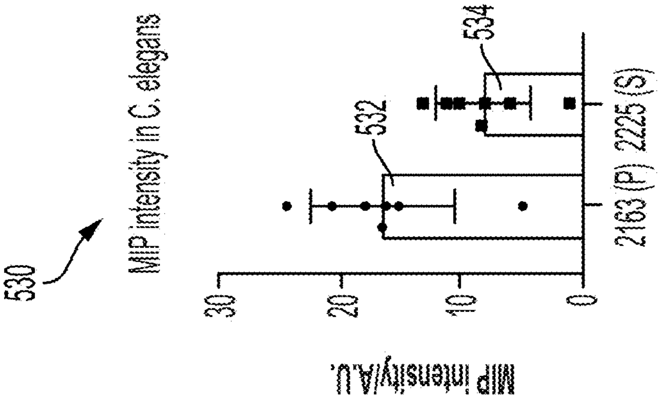
FIG. 5*g* is a graph showing quantification of the MIP signal intensity from Casp-CN-(P) (532) and Casp-CN-(S) in the UV-pretreated and drug-free *C. elegans.*
Figure 5F:
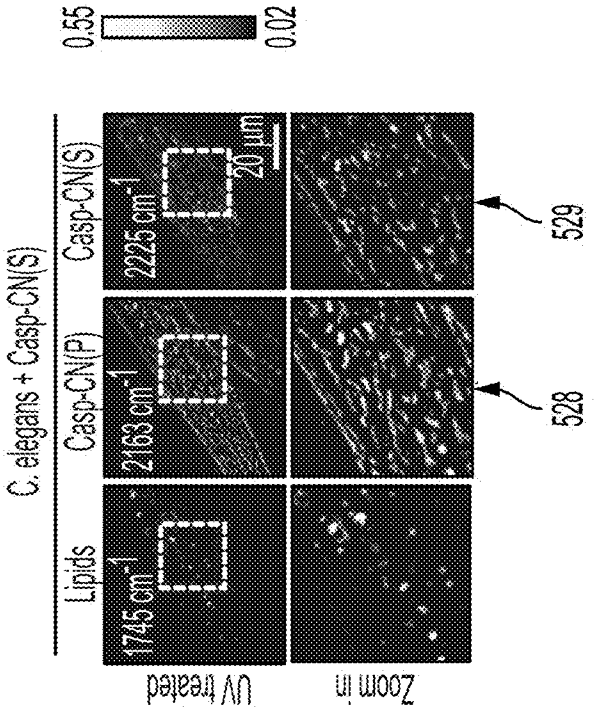
FIG. 5*f* shows MIP imaging of caspase activity profile in UV-pretreated *C. elegans.*
Figure 5E:
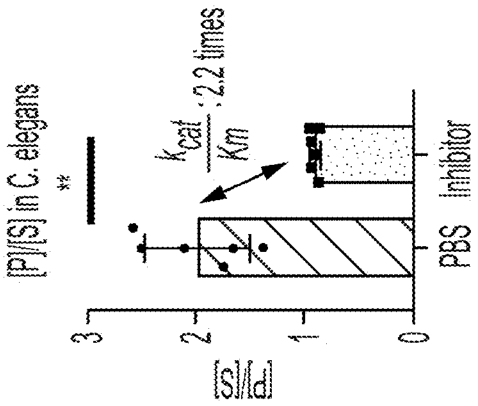
FIG. 5*e* shows statistics of phosphatase [P]/[S] values in the inhibitor-free *C. elegans* and PIC-pretreated *C. elegans.*
Figure 5H:
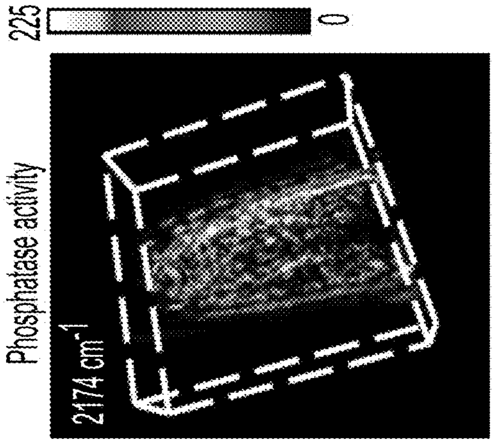
FIGS. 5*h* and 5*i* are 3D reconstructions of phosphatase activity and caspase activity, respectively, in *C. elegans.*
Figure 5I:
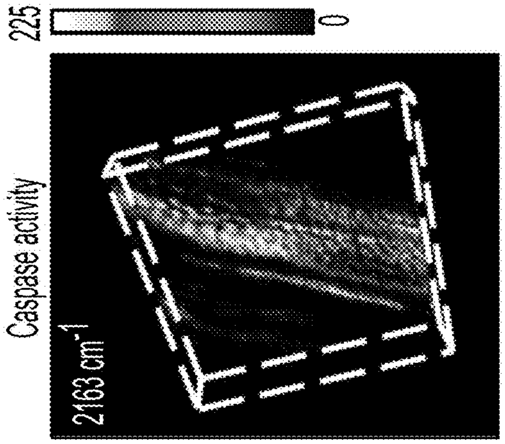
Figure 5J:
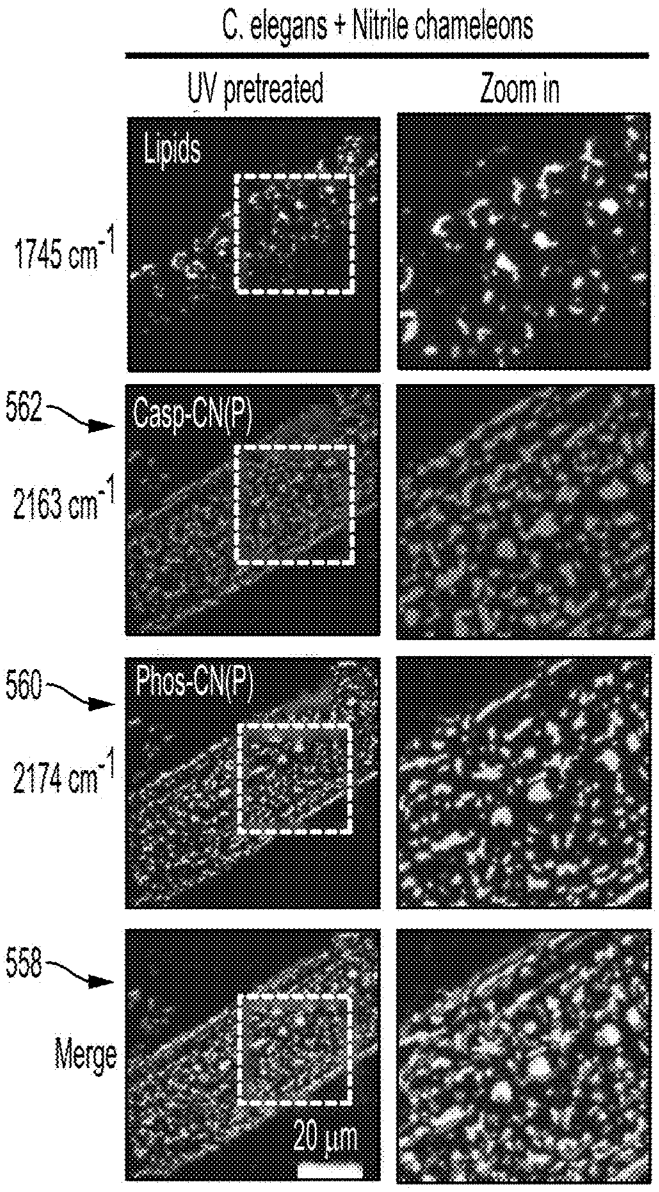
FIG. 5*j* shows images of simultaneous activity mapping of phosphatase and caspase in UV-pretreated *C. elegans.*
Figure 5K:
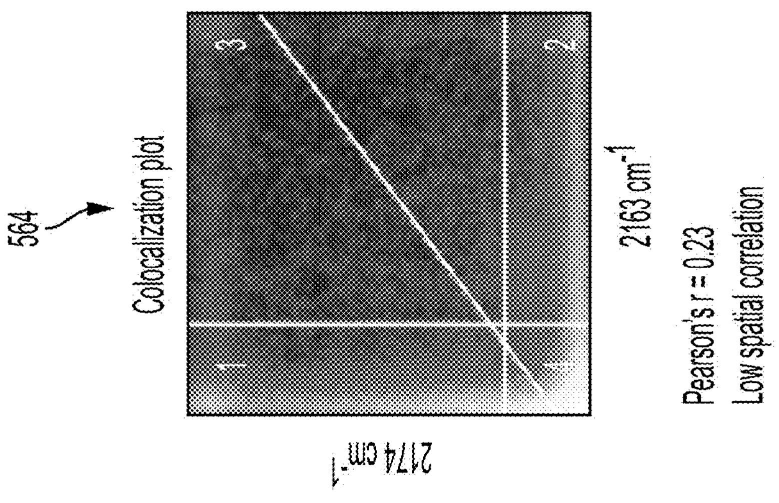
FIG. 5*k* is a colocalization analysis of the mapping in FIG. 5*j*.
Figure 5L:
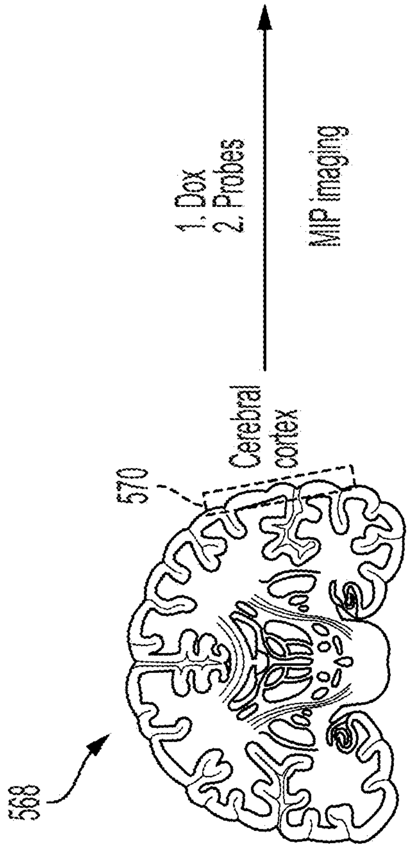
FIG. 5*l* shows a mouse brain, imaged in accordance with the subject technology.
Figure 5M:
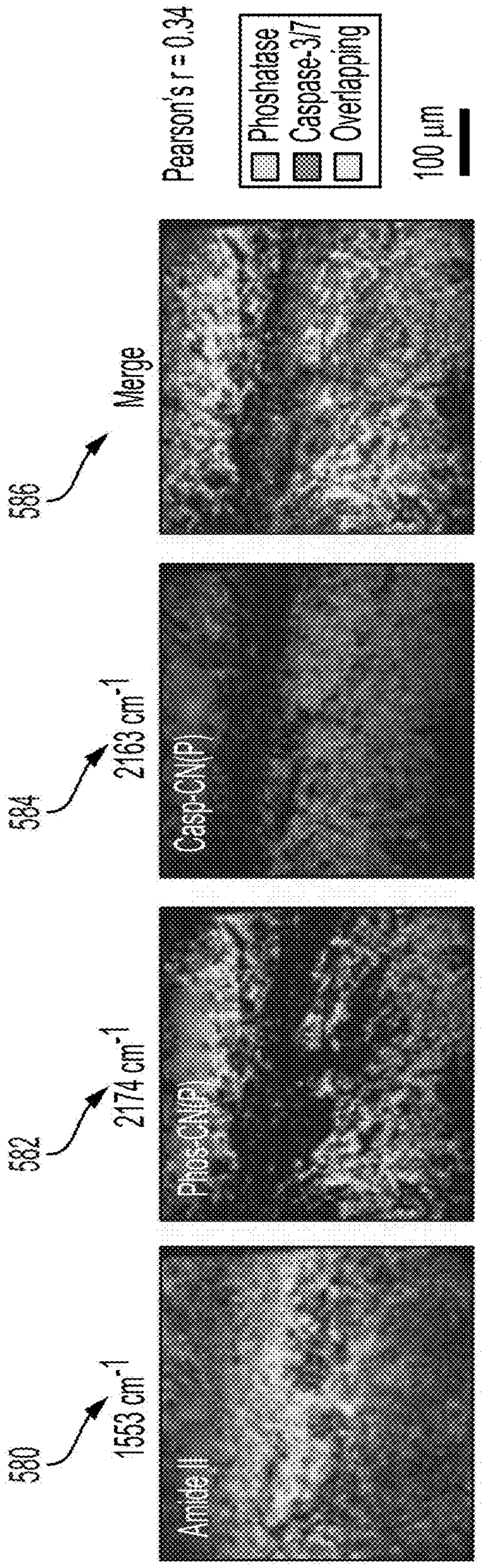
FIG. 5*m* shows simultaneous mapping of phosphatase and caspase activities in Dox-pretreated (1 μM) mouse cerebral cortex sections.

Referring now to FIGS. 5*a*-5*m*, multicolor MIP imaging of nitrile chameleons generates activity maps of caspase and phosphatase inside *C. elegans* and brain tissues. FIG. 5*a* shows MIP imaging of phosphatase profile in living *C. elegans*. FIG. 5*b* is a graph 510 showing quantification of the MIP signal intensity from Phos-CN-(P) (512) and Phos-CN-(S) (514) in the inhibitor-free *C. elegans* (n=6 ('. *elegans*, data are presented as mean±SD). FIG. 5*c* shows MIP imaging of phosphatase activity profile in the PIC-pretreated *C. elegans*. FIG. 5*d* is a graph 516 showing quantification of the MIP signal intensity from Phos-CN-(P) (518) and Phos-CN-(S) (520) in the PIC-pretreated *C. elegans*. (n=6 ('. *elegans*, data are presented as mean±SD). FIG. 5*e* shows statistics of phosphatase [P]/[S] values in the inhibitor-free *C. elegans* and PIC-pretreated *C. elegans* (n=6 ('. *elegans*, data are presented as mean±SD). Statistics was performed by paired t-test (two-tailed) without adjustments for multiple comparisons. The p value is 0.0019. $p \leq 0.01$. FIG. 5***f* shows MIP imaging of caspase activity profile in UV-pretreated *C. elegans*. FIG. 5*g* is a graph 530 showing quantification of the MIP signal intensity from Casp-CN-(P) (532) and Casp-CN-(S) (534) in the UV-pretreated and drug-free *C. elegans* (n=6 ('. *elegans*, data are presented as mean±SD). FIGS. 5*h* and 5*i* are 3D reconstruction of phosphatase activity (image 550 of FIG. 5*h*) and caspase activity (image 552 of FIG. 5*i*) in *C. elegans*. FIG. 5*j* shows simultaneous activity mapping of phosphatase and caspase in UV-pretreated *C. elegans*. The experiment was repeated independently at least 10 times with similar results. FIG. 5*k* is a colocalization analysis of the mapping in FIG. 5*j*. FIGS. 5*l* and 5*m* show simultaneous mapping of phosphatase and caspase activities in Dox-pretreated (1 μM) mouse cerebral cortex sections. The experiment was repeated independently 10 times with similar results. Thus, multicolor MIP imaging of enzyme activities in *C. elegans* and brain tissues were shown.

We explored enzyme activity mapping in *C. elegans* and brain tissues via MIP imaging of the nitrile chameleons. After incubating Phos-CN(S) with *C. elegans*, real-time MIP imaging at 1745 and 2174 $cm^{-1}$ revealed the biodistribution of lipid droplets and Phos-CN(P) which exposed the phosphatase activity profile in *C. elegans* (FIG. 5*a*). While *C. elegans* lack ALP, the intensive MIP signal from the C≡N of Phos-CN(P) at 2174 $cm^{-1}$ and a weaker one from Phos-CN(S) at 2215 $cm^{-1}$ confirm an efficient enzymatic conversion (FIGS. 5*a* and 5*b*), suggesting a high activity from other phosphatase isoenzymes, such as PTP, in *C. elegans*. As controls, MIP contrast is hardly observed in the *C. elegans* without nitrile chameleon treatment. PIC significantly reduces the phosphatase activity in ('. *elegans*, as revealed by the weaker MIP signal from Phos-CN(P) and Phos-CN(S) (FIGS. 5*c* and 5*d*). To avoid cell death due to the cytotoxicity of PIC, the PIC concentration we employed might not completely deplete phosphatase activity in cells and ('. *elegans*, resulting in the remnant of some phosphatase activity. The average [P]/[S] obtained from the PIC-treated *C. elegans* versus one from the inhibitor-free group suggests a 54% decrease in the catalytic efficiency ($k_{cat}/K_M$) of the phosphatase (FIG. 5*e*) in *C. elegans* via PIC treatment. Although the caspase (e. g. CED-3) of *C. elegans* may differ from the one of a human, DEVD works as the substrate. We exposed *C. elegans* to UV radiation to induce apoptosis for caspase activation. After incubating the UV-irradiated *C. elegans* with Casp-CN(S), real-time MIP imaging at 2163 $cm^{-1}$ reveals the activity profile of the caspase in *C. elegans* (images 528 of FIG. 5*f*). The strong MIP signal from Casp-CN(P) and the lower signal from Casp-CN(S) at 2223 $cm^{-1}$ (images 529) confirm a high caspase activity in the UV-treated *C. elegans* (see respective bar lines 532, 534 of FIG. 5*g*). Conversely, faint MIP signals from Casp-CN(P) and Casp-CN(S) were observed in the UV-free *C. elegans*, indicating the existence of a weak caspase activity background in *C. elegans*.

We further reconstructed the 3D activity profiles of phosphatase (image 546 of FIG. 5*h*) and caspase (image 548 of FIG. 5*i*) in the nematode. Besides visualizing the enzyme activity individually, we concurrently mapped the activity of phosphatase and caspase in *C. elegans* through incubating the UV-irradiated *C. elegans* with nitrile chameleons followed by MIP imaging, in the images shown in FIG. 5*j*. The merge channel (558) and colocalization analysis 564 (of FIG. 5*k*, Pearson's r=0.23) show a poor overlapping between the MIP signals from Phos-CN(P) (560) and Casp-CN(P) (562), confirming the identification and differentiation of the activity profiles of diverse enzymes in *C. elegans* by MIP imaging of nitrile chameleons.

We further concurrently mapped the activity of phosphatase and caspase-3/7 in sections of mouse brains. Caspase-3/7 in fresh mouse brains (568 of FIG. 5*l*) were activated through an ex vivo incubation with Dox (1 μM, 24 h), simulating chemotherapy-induced neurotoxicity. After incubating the Dox-treated tissues with nitrile chameleons, MIP imaging (580, 582, 584, 586) produced clear activity maps of phosphatase and caspase-3/7 in the unfixed tissue sections of cerebral cortex 570 (FIGS. 5*l* and 5*m*). MIP images of the phosphatase activity map in the brain slices resemble the pattern of phosphatase histochemistry, which reveals the dense network of capillaries in the cortical mantle. The merged channel and colocalization analysis (586) revealed a low spatial overlapping between Phos-CN (P) (image 582) and Casp-CN(P) (image 584) (Pearson's r=0.34). This supports the capability to identify and differentiate the activity distribution of various enzymes in the cerebral cortex via MIP imaging of nitrile chameleons. In tissues without the treatment of nitrile chameleons serving as controls, little MIP contrast of C≡N is shown.

As such, spatially mapping the activity of multiple enzymes in a living system is significant for elucidating enzymatic functions in health and connections to diseases. Systems and methods are disclosed herein for utilizing an MIP microscopy imaging system for imaging living system. In this disclosure, we discuss the development of nitrile (C≡N)-tagged enzyme activity reporters, named nitrile chameleons for the peak shift between substrate and product. By real-time mid-infrared photothermal imaging of the enzymatic substrates and products at 300 nm resolution, our approach can map the activity distribution of different enzymes and quantitate the relative catalytic efficiency in living cancer cells, *C. elegans*, and brain tissues, enabling direct visualization of caspase-phosphatase interaction during apoptosis. Our method is generally applicable to a broad category of enzymes and heralds the potential of advancing discovery of targets for diagnosis and treatment.

The probes, as described herein, can be molecular probes for characterizing biological activity, such as enzyme activity. While specific exemplary probes are discussed herein, it should be understood that various probes, including enzyme probes, can be used which employ an enzyme substrate and chemical functional group in accordance with the teachings here. In general, a chemical functional group with a spectral shift between 2000 $cm^{-1}$ and 2300 $cm^{-1}$ can be employed. Various chemical functional groups that have been found to be effective include alkyne, nitrile, azide, thiocyanate, and isonitrile groups. In some examples, one or two probes can be used for imaging the sample. In other examples, a larger number of probes can be used. Given that spectral peak width can be around 20 $cm^{-1}$, up to 15 probes may be used in some examples. The enzyme probe can include a self-assembly moiety, which can be a peptide or a peptide derivate, and is generally a hydrophobic peptide. In some embodiments, the chemical functional group is bound to the self-assembly moiety. In some embodiments, the chemical functional group is bound to the enzyme substrate. The probe can also include various enzyme substrates, in accordance with the teachings herein. For example, in some cases, the enzyme substrates include phosphatases, caspases, protein kinases, esterases, and matrix metalloproteases.

All references cited herein are incorporated by reference, as though fully set forth herein. All orientations and arrangements of the components shown herein are used by way of example only. Further, it will be appreciated by those of ordinary skill in the pertinent art that the functions of several elements may, in alternative embodiments, be carried out by fewer elements or a single element. Similarly, in some embodiments, any functional element may perform fewer, or different, operations than those described with respect to the illustrated embodiment. Also, functional elements shown as distinct for purposes of illustration may be incorporated within other functional elements in a particular implementation.

While the subject technology has been described with respect to preferred embodiments, those skilled in the art will readily appreciate that various changes and/or modifications can be made to the subject technology without departing from the spirit or scope of the subject technology. For example, each claim may depend from any or all claims in a multiple dependent manner even though such has not been originally claimed.

What is claimed is:

1. A method of characterizing biological activity in at least one live cell of a sample on a substrate using a mid-infrared photothermal (MIP) system and at least one molecular probe, comprising:
- introducing the at least one molecular probe to the sample;
- generating, with a mid-infrared optical source, a mid-infrared beam, the mid-infrared beam being directed at the sample to induce a thermal effect;
- generating, with a visible light source, a light, the light illuminating the sample on the substrate; and
- collecting, with an optical detector, the light after interaction with the sample and the at least one molecular probe; and
- characterizing biological activity in the sample based on a spectral shift of each of the at least one molecular probe caused by the biological activity,
- wherein the biological activity comprises enzymatic activity, lipid oxidation, level of oxidative stress, or membrane voltage, and
- wherein each molecular probe comprises:
  - a) a substrate, and
  - b) a chemical functional group, and
  - c) has a structure selected from:

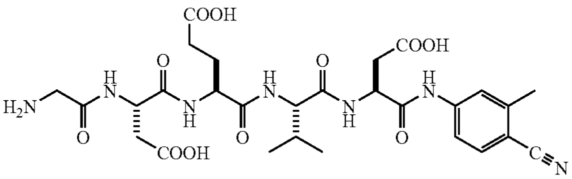

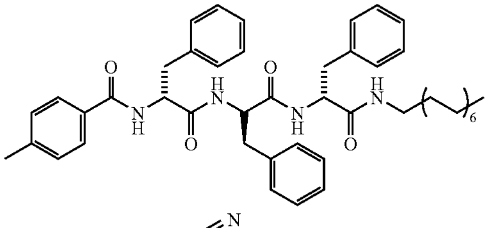

or

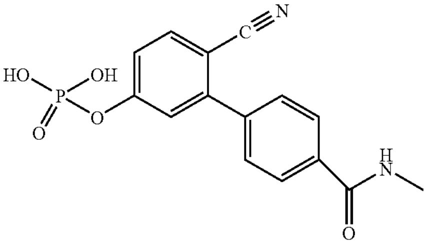

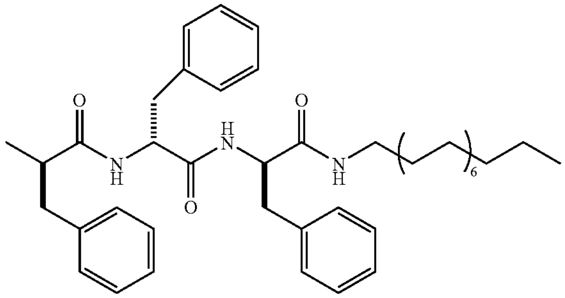

.

2. The method of claim 1, wherein the at least one molecular probe comprises one to two enzyme probes.

3. The method of claim 1, wherein the substrate is an enzyme substrate selected from phosphatases and caspases.

4. The method of claim 1, wherein the cell is an animal cell.

5. The method of claim 4, wherein the animal cell is a human cell.

6. The method of claim 5, wherein the human cell is a cancer cell.

7. The method of claim 6, wherein the cancer cell is a brain cancer cell.

8. The method of claim 6, wherein the cancer cell is a tumor cell.

9. The method of claim 1, wherein collecting light with the optical detector after interaction with the sample is done in the forward and backward directions.

10. The method of claim 1, wherein the light is focused with a water immersion objective lens.

11. A mid-infrared photothermal (MIP) system and at least one molecular probe for characterizing biological activity in at least one live cell of a sample on a substrate, comprising:
- a mid-infrared optical source configured to generate a mid-infrared beam, the mid-infrared beam being directed at the sample to induce a thermal effect;
- a visible light source generating a light, the light illuminating the sample on the substrate; and an optical detector configured to collect the light after interaction with the sample, wherein:

each molecular probe is operable to exhibit a spectral shift in the presence of the biological activity and comprises:

a) a substrate, and b) a chemical functional group, and c) has a structure selected from:

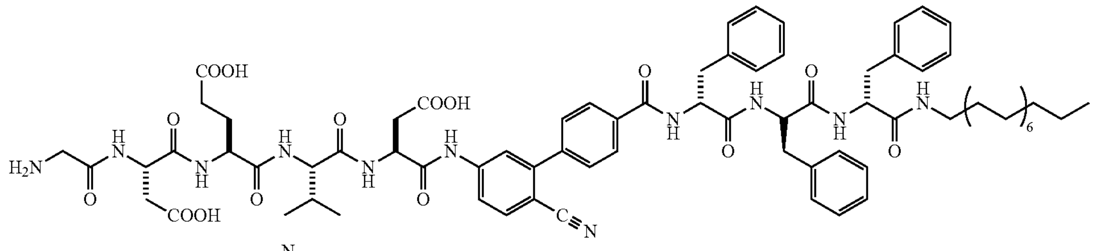

or

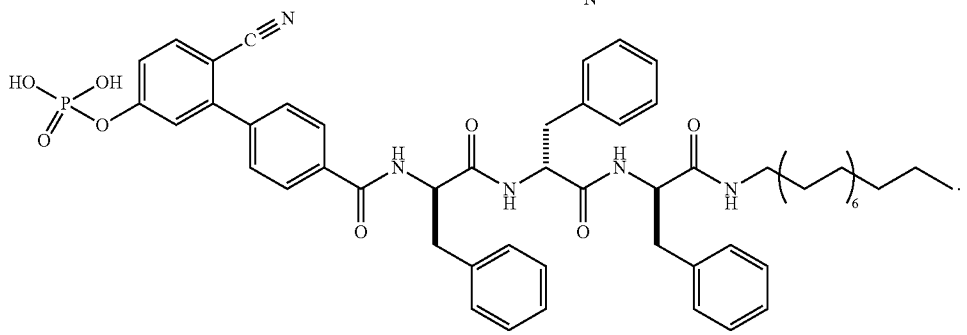

12. The MIP system of claim 11, wherein the at least one molecular probe comprises 2 enzyme probes.

13. The MIP system of claim 11, wherein the cell is one of the following: an animal cell; or a human cell.

14. The MIP system of claim 11, wherein the substrate is an enzyme substrate selected from phosphatases and caspases.

15. The MIP system of claim 11, wherein the MIP system comprises two optical detectors configured to collect light after interaction with the sample, including a first optical detector collecting light in a forward direction and a second optical detector collecting light in a backward direction.

16. The MIP system of claim 11, further comprising a water immersion objective lens configured to focus the light.

* * * * *